United States Patent
Yap et al.

(10) Patent No.: US 9,903,757 B1
(45) Date of Patent: Feb. 27, 2018

(54) ACTIVE MULTI-SPECTRAL SENSOR

(71) Applicant: HRL Laboratories, LLC, Malibu, CA (US)

(72) Inventors: Daniel Yap, Newbury Park, CA (US); Brian Neff, Solana Beach, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 15/275,172

(22) Filed: Sep. 23, 2016

Related U.S. Application Data

(60) Provisional application No. 62/233,109, filed on Sep. 25, 2015.

(51) Int. Cl.
| | |
|---|---|
| *G01J 3/10* | (2006.01) |
| *G01J 3/02* | (2006.01) |
| *G01J 3/42* | (2006.01) |
| *G01N 21/39* | (2006.01) |
| *G01N 21/35* | (2014.01) |
| *G01N 21/94* | (2006.01) |

(52) U.S. Cl.
CPC ............ *G01J 3/108* (2013.01); *G01J 3/0208* (2013.01); *G01J 3/42* (2013.01); *G01N 21/35* (2013.01); *G01N 21/39* (2013.01); *G01N 21/94* (2013.01); *G01J 2003/102* (2013.01); *G01N 2021/399* (2013.01); *G01N 2201/067* (2013.01)

(58) Field of Classification Search
CPC .. G01J 3/0208; G01J 3/108; G01J 3/42; G01J 2003/102; G01N 21/35; G01N 21/39; G01N 21/94; G01N 2021/399; G01N 2201/067
See application file for complete search history.

(56) References Cited

U.S. PATENT DOCUMENTS

| | | | | |
|---|---|---|---|---|
| 5,790,242 A | * | 8/1998 | Stern | G01S 17/89 356/4.04 |
| 9,230,302 B1 | | 1/2016 | Owechko et al. | |
| 2005/0271258 A1 | * | 12/2005 | Rowe | G06K 9/00046 382/124 |
| 2006/0038705 A1 | | 2/2006 | Brady et al. | |
| 2007/0242327 A1 | * | 10/2007 | Powell | G02B 26/10 359/204.1 |
| 2008/0106983 A1 | * | 5/2008 | Takemoto | G02F 1/29 369/44.23 |
| 2011/0270092 A1 | * | 11/2011 | Kang | A61B 5/0071 600/476 |

(Continued)

OTHER PUBLICATIONS

J. R. Castro-Suarez, Y. S. Pollock and S. P. Hernandez-Rivera, "Explosives detection using quantum cascade laser spectroscopy," Proceedings SPIE vol. 8710, paper 871010 (2013).

(Continued)

*Primary Examiner* — Mark R Gaworecki
(74) *Attorney, Agent, or Firm* — Ladas & Parry

(57) ABSTRACT

A sensor includes a plurality of transmitter units, a photodetector, and an optical system coupled to the plurality of transmitter units and the photodetector. Each of the transmitter units simultaneously transmits a light beam having a plurality of wavelengths, the optical system directs the light beam from each of the transmitter units onto a same illuminated spot on a probed surface, and the optical system collects light from the same illuminated spot and directs the light to the photodetector.

23 Claims, 20 Drawing Sheets
(20 of 20 Drawing Sheet(s) Filed in Color)

(56) References Cited

U.S. PATENT DOCUMENTS

| | | | |
|---|---|---|---|
| 2011/0279682 A1 | 11/2011 | Li et al. | |
| 2013/0012794 A1* | 1/2013 | Zeng | A61B 1/00186 600/328 |
| 2014/0009752 A1* | 1/2014 | Cronin | H01L 27/14601 356/71 |
| 2014/0247372 A1 | 9/2014 | Byren | |
| 2015/0205992 A1* | 7/2015 | Rowe | G06K 9/2018 382/124 |
| 2016/0290927 A1* | 10/2016 | Buczkowski | G01N 21/6489 |

OTHER PUBLICATIONS

J. D. Suter, B. Bernacki and M. C. Phillips, "Spectral and angular dependence of mid-infrared diffuse scattering from explosives residues for standoff detection using external cavity quantum cascade lasers," Applied Physics B, 108:965-974, Sep. 15, 2012.

M. C. Phillips and B. E. Ber nacki, "Hyperspectral microscopy of explosives particles using an external cavity quantum cascade laser," Optical Engineering, 52(6), 061302 (Jun. 2013).

F. Fuchs, et al., "Imaging standoff detection of explosives using widely tunable midinfrared quantum cascade lasers," Optical Engineering, 49(11), 111127 (Nov. 2010).

B. G. Lee, et al., "DFB quantum cascade laser arrays," IEEE Journal of Quantum Electronics, 45(5), 554 (May 2009).

B. G. Lee, et al., "Beam combining of quantum cascade laser arrays," Optics Express, 17(18), 16216 (2009).

A. K. Goyal, et al., "Dispersion-compensated wavelength beam combining of quantum-cascade-laser arrays," Optics Express, 19(27), 26725 (Dec. 2011).

S. Slivken, et al., "Sampled grating, distributed feedback quantum cascade lasers with broadband tenability and continuous operation at room temperature," Applied Physics Letters, v.100, 261112 (2012).

S. Menzel, et al., "Quantum cascade laser master-oscillator power-amplifier with 1.5 W output power at 300 K," Optics Express, 19(17), 16229 (2011).

P. S. Wijewarnasuriya, "Nonequilibriium operation of long wavelength HgCdTe photo detectors for higher operating temperatures," Proceedings SPIE vol. 7780, 77800A (2010).

A. M. Itsuno, J. D. Phillips and S. Velicu, "Predicted performance improvement of Auger-suppresed HgCdTe photodiodes and p-n heterojunction detectors," IEEE Transactions on Electron Devices, 58(2), 501 (Feb. 2011).

G. L. Abbas, V. W. S. Chan and T. K. Yee, "A dual-detector optical heterodyne receiver for local oscillator noise suppression," Journal of Lightwave Technology, 3(5), 1110 (Oct. 1985).

"LaserSense™: Compact Gas Detection System," webpage available at: http://www.blockeng.com/products/lasersense.html, accessed on Sep. 23, 2016 at 10:29 AM.

"LaserWarn™: Open-Path Chemical Detection System" webpage available at: http://www.blockeng.com/products/laserwarn.html, accessed on Sep. 21, 2016 at 3:25 PM.

"LaserTune™ Widely Tunable Mid-Infrared Laser Source" webpage available at: http://www.blockeng.com/products/lasertune.html, accessed on Sep. 21, 2016 at 3:28 PM.

"Ultra-broadly tunable mid-IR external-cavity CW/Pulsed MIRcat™ laser system" product brochure, Feb. 29, 2016, available at: http://www.daylightsolutions.com/scientific-instruments/sci-products/sci-lasers/mircat.htm, accessed on Sep. 21, 2016.

"OmniLux™ Multiple Tunable QCL System" webpage available at http://www.pranalytica.com/products-services/omnilux.php, accessed on Sep. 21, 2016 at 3:47 PM.

Aharon, Elad, and Bruckstein, "The K-SVD: An Algorithm for Designing of Overcomplete Dictionaries for Sparse Representation", the IEEE Trans. on Signal Processing, vol. 54, No. 11, pp. 4311-4322, Nov. 2006.

Cardoso and Souloumiac in "Blind beamforming for non-Gaussian signals," IEE Proceedings-F v. 140, No. 6, Dec. 1993, p. 362.

Choi et al. in Blind Source Separation and Independent Component Analysis, Neural Information Processing—Letters and Reviews vol. 6, No. 1, Jan. 2005.

Larcom and Coffman, "Foveated Image Formation through Compressive Sensing," Image Analysis & Interpretation (SSIAI), 2010 IEE Southwest Symposium. May 23-25, 2010, Austin, TX, USA, pp. 145-148.

Sharma and Nayak, "Region of Interest Compressed Sensing," ISMRM Workshop on Data Sampling and Image Reconstruction, Jan. 2009, Sedona.

Zelnik-Manor, Rosenblum, Eldar and, "Sensing Matrix Optimization for Block-Sparse Decoding." IEEE Transactions on Signal Processing 59(9): 4300-4312 (Sep. 2011).

J. R. Quinlan in tutorials and references available at URL: http://www.ruleguest.com visited on Feb. 24, 2017.

U.S. Appl. No. 15/280,575 (unpublished) Application and Office Actions.

U.S. Appl. No. 15/283,358 (unpublished) Application and Office Actions.

U.S. Appl. No. 15/445,782 (unpublished) Application and Office Actions.

U.S. Appl. No. 14/204,028 (now U.S. Pat. No. 9,230,302) Notice of Allowance dated Aug. 28, 2015.

U.S. Appl. No. 15/445,782, filed Feb. 28, 2017, Yap et al.

U.S. Appl. No. 15/280,575, filed Sep. 29, 2016, Owechko et al.

U.S. Appl. No. 15/283,358, filed Oct. 1, 2016, Rao et al.

\* cited by examiner

| Laser Design | Wavenumber Range (cm⁻¹) | Wavelength range (μm) | Wavenumber increment (cm⁻¹) | Wavenumber (cm⁻¹) & wavelength (nm) increment |
|---|---|---|---|---|
| 1 | 1600-1500 | 6.25-6.67 | 5 | 19.6-22.2 | 0.0196-0.0222 |
| 2 | 1500-1400 | 6.67-7.14 | 5 | 22.3-25.4 | 0.0223-0.0254 |
| 3 | 1400-1300 | 7.14-7.69 | 5 | 25.7-29.5 | 0.0257-0.0295 |
| 4 | 1300-1200 | 7.69-8.33 | 5 | 29.7-34.5 | 0.0297-0.0345 |
| 5 | 1200-1100 | 8.33-9.09 | 5 | 34.9-41.1 | 0.0349-0.0411 |
| 6 | 1100-1000 | 9.09-10.0 | 5 | 41.5-49.8 | 0.0415-0.0498 |
| 7 | 1000-0900 | 10.0-11.1 | 5 | 50.3-61.4 | 0.0503-0.0614 |
| 8 | 0900-0800 | 11.1-12.5 | 5 | 62.1-77.6 | 0.0621-0.0776 |
| 9 | 3100-3000 | 3.23-3.33 | 5 | 05.2-05.5 | 0.0052-0.0055 |
| 10 | 3000-2900 | 3.33-3.45 | 5 | 05.6-05.9 | 0.0056-0.0059 |

FIG. 5A

| Laser Design | Wavenumber Range (cm⁻¹) | Wavelength range (nm) | Wavenumber Increment (cm⁻¹) | Wavelength Increment (nm) |
|---|---|---|---|---|
| 1 | 1471-1306 | 6800-7655 | 9.7 | 45 |
| 2 | 1299-1174 | 7698-8515 | 7.2 | 43 |
| 3 | 1169-1071 | 8556-9335 | 5.6 | 41 |
| 4 | 1067-0989 | 9374-10115 | 4.4 | 39 |
| 5 | 0985-0921 | 10152-10855 | 3.6 | 37 |
| 6 | 0918-0865 | 10890-11555 | 2.9 | 35 |

FIG. 5B

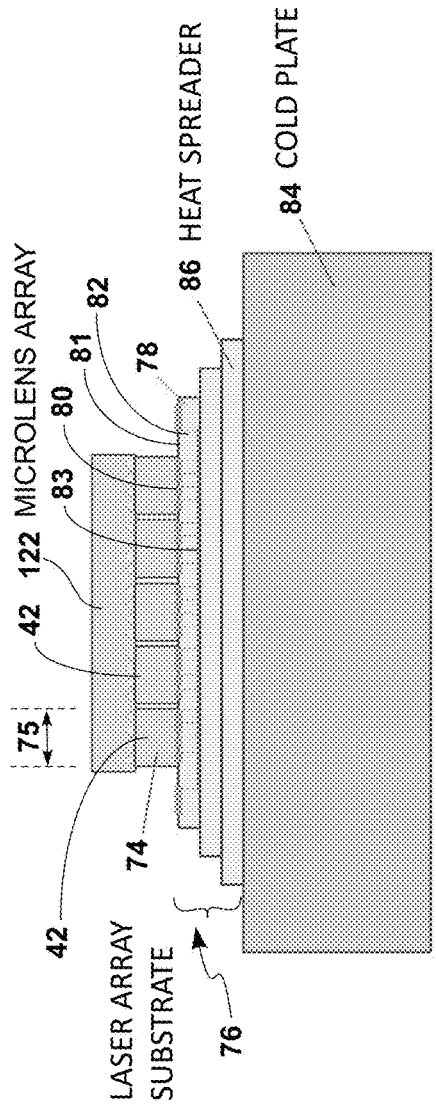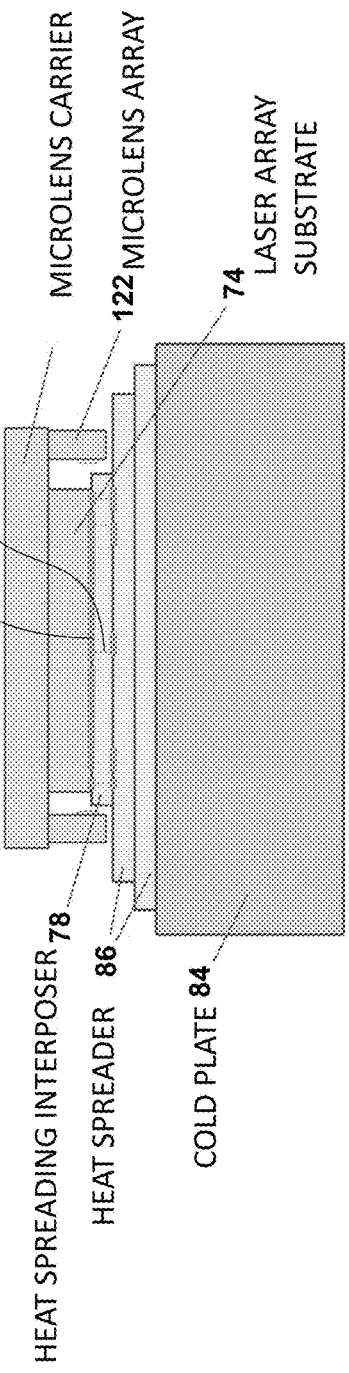

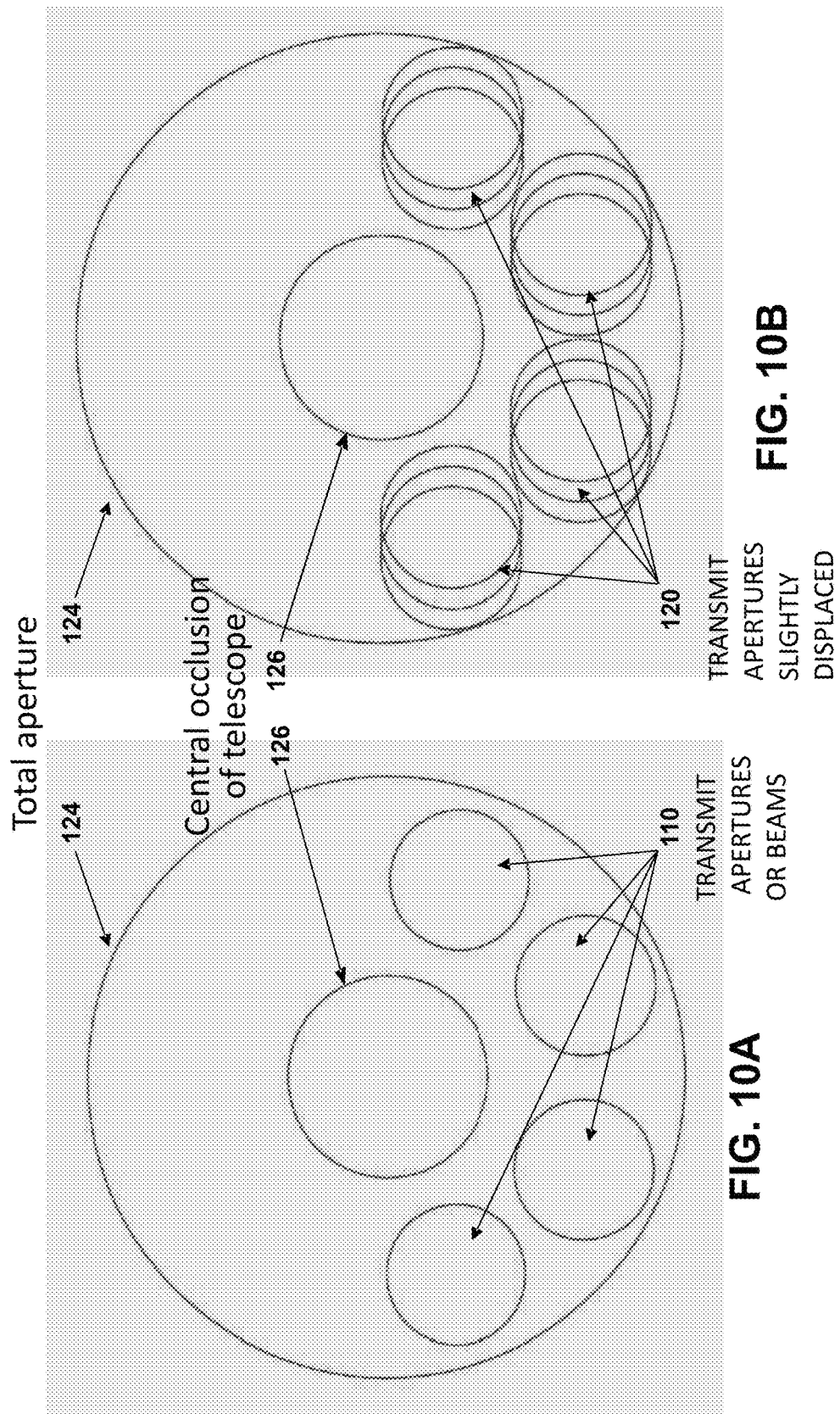

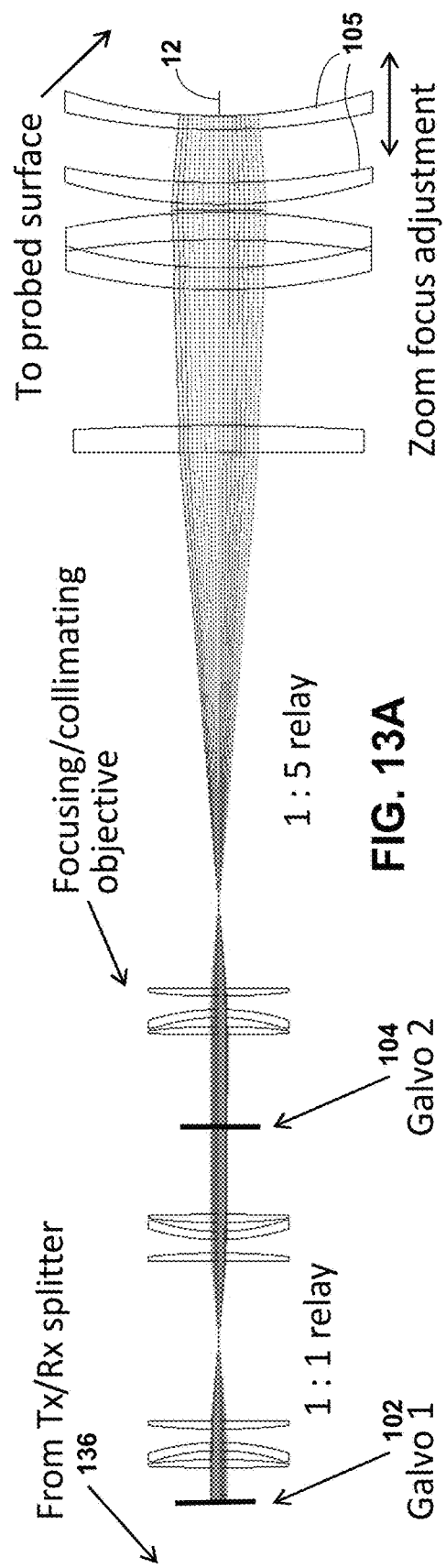
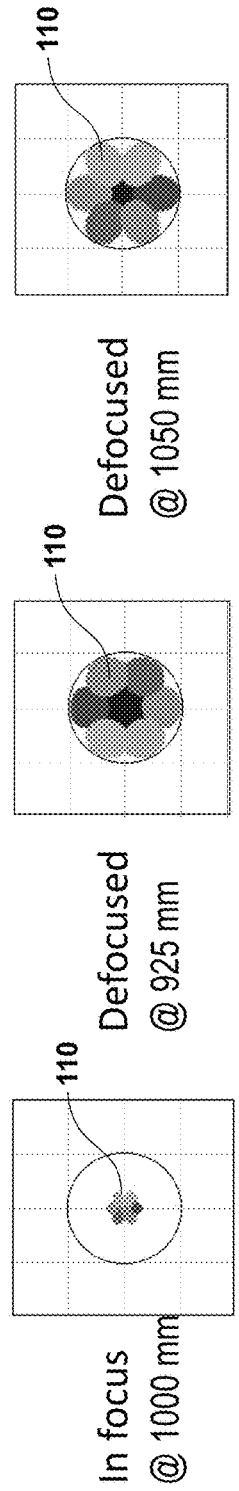
FIG. 13A
FIG. 13C In focus @ 1000 mm
FIG. 13D Defocused @ 925 mm
FIG. 13E Defocused @ 1050 mm

ACTIVE MULTI-SPECTRAL SENSOR

CROSS REFERENCE TO RELATED APPLICATIONS

This application relates to and claims the benefit of priority from U.S. Provisional Patent Application No. 62/233,109, filed on Sep. 25, 2015, which is incorporated herein by reference as though set forth in full.

STATEMENT REGARDING FEDERALLY SPONSORED RESEARCH OR DEVELOPMENT

None

FIELD

This disclosure relates to sensors and active spectrometers.

BACKGROUND

Spectrometers are used to measure the properties of light for a variety of applications including environmental or chemical analysis.

An example of a prior art sensor is the LaserSense™ system, described in Reference [13] listed below, which is incorporated herein by reference. Reference [1] listed below, which is incorporated herein by reference, describes the use of such a system, and in particular a LaserScan™ system for detection of solid residues on a probed surface. Another example is the LaserWarn™ system, described in Reference [14] listed below, which is incorporated herein by reference.

These systems contain a laser source of tunable wavelength or wavenumber and a photodetector. Light of only one wavenumber is transmitted at a given time and the single-wavelength light is directed in a collimated beam toward a probed surface. Light from the vicinity of the probed surface is then collected and detected by a photodetector in the system. The laser light for the LaserScan™ system, referenced in Reference [1], can be tuned over a 600 $cm^{-1}$ span, for example, between 1430 and 830 $cm^{-1}$ and transmits short pulses of relatively low average power (0.5-10 mW). The pulses are produced at a rate of 200 kHz. This sensor transmits an output beam of approximately 2 mm×4 mm size and a beam divergence of 5 mrad.

An active spectrometer with laser illumination also can be constructed from a combination of a laser source with tunable output wavenumber and a separate photodetector or a separate infrared imager having an array of photodetectors. Examples of such spectrometers are described in References [2], [3] and [4], which are incorporated herein by reference. Tunable laser sources, which typically have one or more quantum cascade lasers, are available such as the LaserTune™ system, described in Reference [15] listed below, which is incorporated herein by reference. Other such systems include the MIRcat™ system, described in Reference [16] listed below, which is incorporated herein by reference, and the OmniLux™ system described in Reference [17] listed below, which is incorporated herein by reference. All of these laser sources output laser light having only one wavenumber or wavelength at a time, so that only one wavenumber or wavelength is transmitted at any one time. The photodetector can be thermoelectrically (TE) cooled to a temperature as low as 195K or cryogenically cooled to liquid nitrogen ($LN_2$) temperatures (~77-80K).

A disadvantage of the prior laser sources is that the output power can vary by almost one order of magnitude as the wavelength is tuned. Another disadvantage is that it can take one second or more to obtain a spectrum of 600 $cm=^1$ spectral span. These prior spectrometers have external-cavity lasers that mechanically move an optical element such as a grating or a mirror in the laser cavity to accomplish the wavelength tuning. Also, these prior spectrometers do not include a built-in means to spatially move the beam of output light and instead obtain spatially distinguishable spectra over a large area by illuminating the entire area with a fixed beam and then using an infrared imager that has an array of multiple photodetectors to provide the needed spatial discrimination. Thus, since the illuminating light is spread out over the large area, the illumination power at any given portion of the probed surface is low and the acceptable standoff distance is small (typically 0.5 to 2 meters).

Another prior tunable laser source, described in Reference [5] listed below, which is incorporated herein by reference, has an array of distributed feedback (DFB) lasers for which each DFB laser is designed to emit light of a slightly different wavelength. The desired output wavelength for the array is obtained by switching on only one DFB laser at a time. A given laser of the array is switched on by increasing its drive current to a value exceeding the lasing-threshold current of that laser. The threshold current and slope efficiency of output power vs drive current of the different lasers in an array are different. Thus, the output power of the array can change as the wavelength of the light emitted is changed, which is an undesirable characteristic for a spectrometer. The outputs from the various lasers of an array can be combined into a single optical beam, using a cascade to two gratings, so that the same spot on a probed surface continues to be illuminated as the wavelength of the light is changed, as described in References [6] and [7] listed below, which are incorporated herein by reference.

Prior spectrometers having a laser array activate only one laser and wavelength or wave number at a time and produce a time-varying wavelength scan, as described in References [5] and [6] listed below, which are incorporated herein by reference, because in the prior art, the photodetectors do not have any means to distinguish the wavelength of the light it detects.

REFERENCES

The following references are incorporated by reference as though forth in full.

[1] J. R. Castro-Suarez, Y. S. Pollock and S. P. Hernandez-Rivera, "Explosives detection using quantum cascade laser spectroscopy," Proceedings SPIE Vol. 8710, paper 871010 (2013).

[2] J. D. Suter, B. Bernacki and M. C. Phillips, "Spectral and angular dependence of mid-infrared diffuse scattering from explosives residues for standoff detection using external cavity quantum cascade lasers," Applied Physics B, 108:965-974 (2012).

[3] M. C. Phillips and B. E. Bernacki, "Hyperspectral microscopy of explosives particles using an external cavity quantum cascade laser," Optical Engineering, 52(6), 061302 (June 2013).

[4] F. Fuchs, et al., "Imaging standoff detection of explosives using widely tunable midinfrared quantum cascade lasers," Optical Engineering, 49(11), 111127 (November 2010).

[5] B. G. Lee, et al., "DFB quantum cascade laser arrays," IEEE Journal of Quantum Electronics, 45(5), 554 (May 2009).
[6] B. G. Lee, et al., "Beam combining of quantum cascade laser arrays," Optics Express, 17(18), 16216 (2009).
[7] A. K. Goyal, et al., "Dispersion-compensated wavelength beam combining of quantum-cascade-laser arrays," Optics Express, 19(27), 26725 (December 2011).
[8] S. Slivken, et al., "Sampled grating, distributed feedback quantum cascade lasers with broadband tenability and continuous operation at room temperature," Applied Physics Letters, v. 100, 261112 (2012).
[9] S. Menzel, et al., "Quantum cascade laser master-oscillator power-amplifier with 1.5 W output power at 300 K," Optics Express, 19(17), 16229 (2011).
[10] P. S. Wijewarnasuriya, "Nonequilibriium operation of long wavelength HgCdTe photo detectors for higher operating temperatures," Proceedings SPIE Vol. 7780, 77800A (2010).
[11] A. M. Itsuno, J. D. Phillips and S. Velicu, "Predicted performance improvement of Auger-suppresed HgCdTe photodiodes and p-n heterojunction detectors," IEEE Transactions on Electron Devices, 58(2), 501 (February 2011).
[12] G. L. Abbas, V. W. S. Chan and T. K. Yee, "A dual-detector optical heterodyne receiver for local oscillator noise suppression," Journal of Lightwave Technology, 3(5), 1110 (October 1985).
[13] LaserSense™ system
[14] LaserWarn™ system
[15] LaserTune™ system
[16] MIRcat™ system
[17] OmniLux™ system What is needed is an improved active multi-spectral sensor or spectrometer. The embodiments of the present disclosure answer these and other needs.

SUMMARY

In a first embodiment disclosed herein, a sensor comprising a plurality of transmitter units, a photodetector, and an optical system coupled to the plurality of transmitter units and the photodetector, wherein each of the transmitter units simultaneously transmits a light beam having a plurality of wavelengths, wherein the optical system directs the light beam from each of the transmitter units onto a same illuminated spot on a probed surface, and wherein the optical system collects light from the same illuminated spot and directs the light to the photodetector.

In another embodiment disclosed herein, a multi-spectral sensor comprises a plurality of laser devices each comprising a laser section having a light output, an optical amplifier coupled to the laser section, and an optical modulator coupled to the optical amplifier, wherein the light output of each respective laser section of the plurality of laser devices has a respective wavelength that is different from a wavelength of the light output from each other laser section of the plurality of laser devices, wherein each respective optical modulator of the plurality of laser devices is configured to modulate the light output of a respective laser section with a respective modulation frequency that is different from a modulation frequency of each other optical modulator of the plurality of laser devices, and wherein the multi-spectral sensor is configured so that the plurality of laser devices simultaneously transmit a plurality of light beams, each respective light beam modulated with a respective modulation frequency, and a photodetector for detecting received light, and a channelizer coupled to the photodetector, the channelizer having a plurality of receiver outputs, wherein each respective receiver output of the plurality of receiver outputs is derived using one of the respective modulation frequencies, and wherein each respective receiver output corresponds to one of the respective wavelengths.

In yet another embodiment disclosed herein, a method of sensing comprises simultaneously transmitting a light beam from each of a plurality of transmitter units, wherein each light beam comprises a plurality of wavelengths, directing the light beam from each of the transmitter units onto a same illuminated spot on a probed surface using an optical system, collecting light from the same illuminated spot and directs the collected light to a photodetector, and detecting the collected light using the photodetector.

These and other features and advantages will become further apparent from the detailed description and accompanying figures that follow. In the figures and description, numerals indicate the various features, like numerals referring to like features throughout both the drawings and the description.

BRIEF DESCRIPTION OF THE DRAWINGS

The patent or application file contains a least one drawing executed in color. Copies of this patent or patent application publication with color drawings will be provided by the office upon request and payment of the necessary fee.

FIGS. 5A and 5B show examples of wavenumber and wavelength ranges covered by the laser devices that have a uniform wavenumber increment for the entire array, and uniform wavelength increment only for devices in an array substrate, respectively, in accordance with the present disclosure;

FIGS. 7A and 7B show a multi-function sub-mount and laser array with a microlens array in accordance with the present disclosure;

FIGS. 10A and 10B show a front aperture showing the locations of the four Tx apertures and the area for collecting receive light coupled to the photodetector in accordance with the present disclosure;

FIGS. 13A and 13B show an Illustration of a configuration that has refractive-optics lens elements at the front-end of the sensor, showing in FIG. 13A an example with a 1-to-5 relay with zoom focus and in FIG. 13B an example having three front-end apertures in accordance with the present disclosure;

FIGS. 13C, 13D and 13E show an example of a sensor that has 7 Tx apertures in accordance with the present disclosure.

DETAILED DESCRIPTION

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

Figure 1:
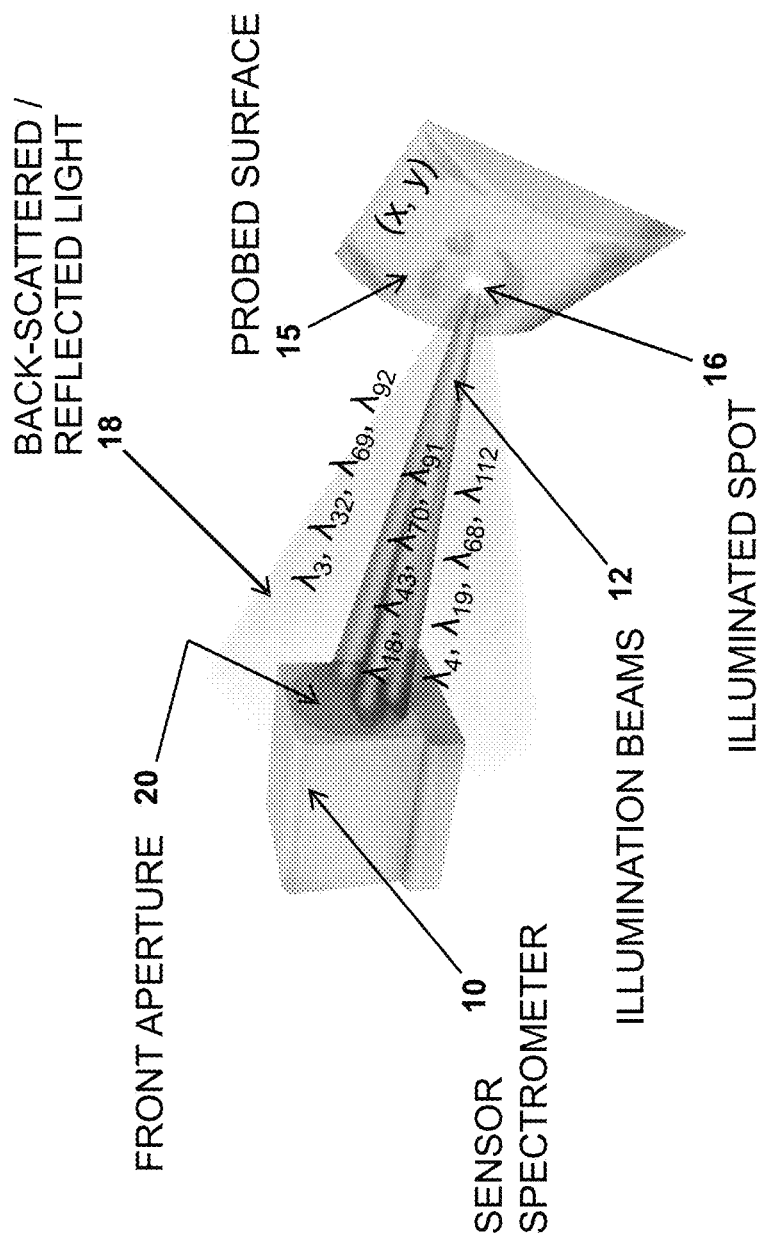
FIG. 1 shows an active spectrometer illuminating a probed surface with beams of multi-wavelength laser light and collecting light back-scattered and reflected from that probed surface in accordance with the present disclosure.
Figure 2:
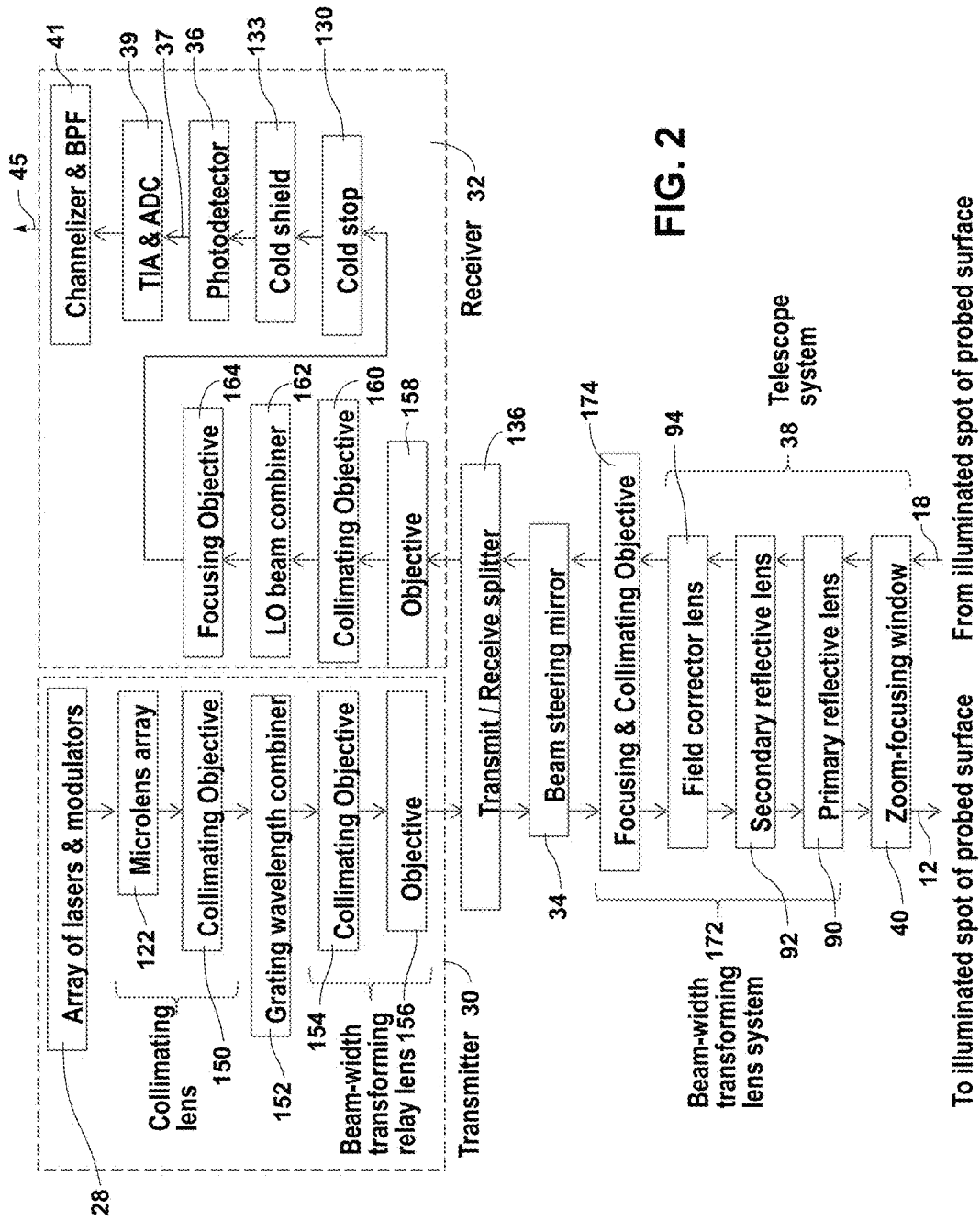
FIG. 2 shows a block diagram showing optical and electrical interconnection between components in an embodiment of a sensor in accordance with the present disclosure.

The present disclosure describes a sensor 10, as shown in FIG. 1, that illuminates and probes a surface with laser light having multiple wavelengths or wavenumbers and measures the dependence of the light reflected or backscattered from the illuminated surface for the wavelength or wavenumber of that light. The sensor 10 has one or more Transmit (Tx) apertures from which the illumination light is transmitted, with each Tx aperture transmitting a beam of multi-wavelength light 12 supplied from an array of laser devices. The one or more beams of multi-wavelength light 12 are overlapped onto the same illuminated spot 16 at the probed surface 15. The sensor 10 also has an aperture through which the light back-scattered or reflected 18 from the probed surface 15 is received. That received light is coupled to one or more photodetectors 36, as shown in FIG. 2. The sensor has an optical system that couples light from multiple laser sources to the Tx apertures and also couples light from the Receive (Rx) aperture to the one or more photodetectors 36. The laser sources are located at an image plane of the optical system and the probed surface 15 generally is located at another focal plane of the optical system. Likewise, the one or more photodetectors 36 are located at an image plane of the optical system and the probed surface 15 is located at another image plane of the optical system. The size of the photodetectors 36 is selected to constrain the one or more photodetectors 36 to collect light only from the illuminated spot 16. Thus, the sensor 10 has maximum sensitivity to the light at the various illumination wavelengths and to the light that is reflected or back-scattered from the illuminated spot 16 on the probed surface 15. The sensor 10 also includes an optical-beam steering mechanism 34 that steers the laser light to be transmitted to the probed surface 15 and moves the illuminated spot 16 to different regions of the probed surface 15. The optical-beam steering mechanism 34 also steers the area of the probed surface 15 that is observed by the one or more photodetectors 36, so that those photodetectors 36 detect light only from the illuminated spot 16.

Figure 3:
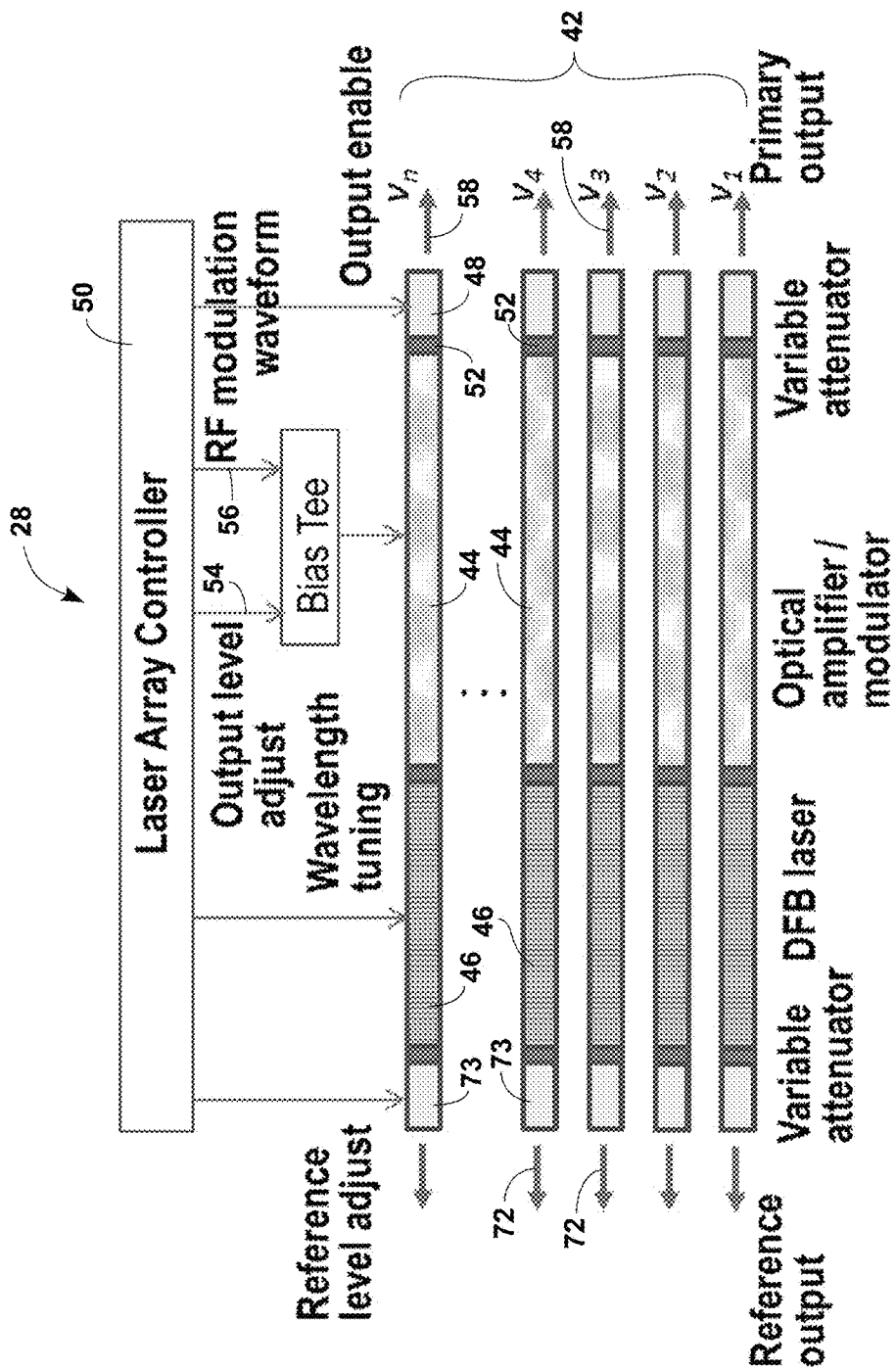
FIG. 3 shows an arrayed laser source with each laser source emitting light of a different wavelength or wavenumber in accordance with the present disclosure.

In contrast to prior active spectrometers that likewise illuminate a surface with light provided by the spectrometer, each laser device 42, as shown in FIG. 3, in the disclosed sensor also includes an optical amplifier 44 that has a modulator 44 that modulates the intensity of the laser light. The laser device 42 may have multiple sections integrated on the same substrate: a single-wavelength laser section 46, and an optical amplifier and modulator section 44. Different laser sources 46 of an array 42 can produce different wavelengths of light. The optical modulator section 44 of different laser devices 42 modulate the different wavelengths of laser light produced by those devices with RF tones 56 of different frequencies. Thus, each wavelength of light transmitted by the sensor can have an RF tone 56 of a different and distinguishing frequency modulated upon that optical wavelength.

One or more photodetectors 36 convert the multi-wavelength light 18 it detects into an RF electrical waveform. This received waveform has multiple RF tones 62 whose amplitudes are associated with the intensities of the photo-detected back-scattered or reflected light 18 at the multiple associated illumination wavelengths. The sensor 10 also has an RF-channelizer circuit 41, as shown in FIG. 2, that produces a set of outputs that indicate the amplitudes of those multiple tones 62, as shown in FIG. 4. Each output of the RF-channelizer circuit 41 is a value that indicates the intensity of the photo-detected light of a given illumination wavelength that is back-scattered or reflected from the probed surface 15.

In some embodiments, the disclosed sensor has multiple, separate Tx apertures 110, as shown in FIGS. 10A and 10B, from which beams of the illumination light 12 are transmitted, in contrast to prior active spectrometers which have a single Tx aperture. The multiple beams 12 from these multiple Tx apertures 110 are overlapped onto the same illuminated spot 16 at the probed surface 15. Each Tx aperture 110 of the disclosed sensor transmits a beam of multi-wavelength light 12 supplied from an array of laser devices 42. As a result, the light on the illuminated spot 16 can contain a large number of simultaneous wavelengths and the optical power at each wavelength can be high while still keeping the optical power level at the Tx apertures 110 of the sensor below the limit for eye-safety (which is 0.1 W/cm$^2$ for exposure durations of 10 seconds or longer for light of 3 µm wavelength or longer).

In some embodiments, the beam steering mechanism 34, as shown in FIG. 2, is controlled such that the length of time during which the illuminated spot 16 dwells at a particular location of the probed surface 15 is sufficiently short that the intensity of the multi-wavelength light 12 in the illuminated spot 16 remains below the eye-safety limit. For example, assume the size of the illuminated spot 16 is 1 cm$^2$ and the overall size of the probed surface 15 is 1 m$^2$. Assume, also, that the entire probed surface 15 is scanned in a time of 10 seconds, which means the dwell time for each spot 16 is 1 msec. For this example, the power of the multi-wavelength light in the illuminated spot 16 may be as high as 100 W and still be eye-safe. If the illuminated spot 16 dwells at a particular location for a longer time, the eye-safe power density is reduced, such as to 10W for a dwell time of 20 msec. Consider, for example, the case with 10 W illuminating the illuminated spot 16 that is produced by overlapping 4 beams of multi-wavelength light 12. Each beam can produce 2.5 W, for this example. Thus, to be eye safe, each of the 4 Tx apertures 110 needs to have an area of 25 cm$^2$ or larger, which may be achieved, for example, by a circular aperture of 5.642 cm diameter or larger.

In some embodiments, the lasers 46 of this sensor 10 emit light of long-wave infrared (LWIR) wavelengths. In some embodiments, the lasers 46 of this sensor also emit light of mid-wave infrared (MWIR) wavelengths. In some embodiments, the lasers 46 of this sensor emit light of short-wave infrared (SWIR) wavelengths.

The sensor 10 of the present disclosure can detect the presence of a given chemical based on its infrared absorbance/reflectance signature. Many chemicals such as explosives and highly energetic materials, chemical warfare agents and simulants, narcotics and other drugs, biological products, and industrial chemicals have characteristics absorbance/reflectance at specific wavelengths or wavenumbers in the LWIR, MWIR and SWIR spectral ranges that can be used to identify the presence of those chemicals based on their infrared (IR) signatures. Since this sensor 10 makes use of collimated beams of laser light, the sensor can be used for standoff detection of trace residues of such chemicals. The standoff distance can be greater than 10 meters and, for some applications, even greater than 100 meters. This sensor can detect the presence of small amounts of solid or liquid chemical residue that may be present on the probed surface as well as dilute amounts of gas-phase chemicals that may be in the optical path between the sensor 10 and the probed surface 15. The sensor can possibly detect solid chemicals even at concentrations as low as 1 $\mu g/cm^2$ and vapor-phase chemicals even at concentrations as low as 0.1 parts-per-billion. This sensor can scan the illuminated spot 16 over an area of the probed surface 15. Thus, in some embodiments, this sensor 10 can produce a multi-spectral spatial map of the probed surface 15. In other embodiments, different areas of the probed surface 15 can be probed with different combinations of illumination wavelengths.

The sensor 10 of the present disclosure illuminates only a small-size spot 16 of the probed surface 15 at a given instance and detects light 18 only from the illuminated spot 16. Thus, the sensor 10 minimizes the effect of clutter that may be associated with light from other areas. Also, this sensor distinguishes between the photo-detected light at the specific illumination wavelengths 12 and photo-detected light at other (non-illuminated) wavelengths. Thus, the sensor can exclude from the output values of the RF-channelizer circuit 41 the reflected or back-scattered light 18 due to passive illumination rather than the active laser illumination 12 and can also exclude the light from black-body radiation. This combination of spatially selectivity plus spectrally selectivity of the sensor is especially important for sensing spectral signatures in the LWIR range, since typical surfaces and surrounding objects, and even portions of the spectrometer itself, have substantial black-body emission in the LWIR wavelength band. The result is improved sensitivity of the sensor for the chemicals to be detected and insensitivity to ambient clutter.

In contrast to the prior art, the active spectrometer 10 of the present disclosure can produce and transmit beams of light 12 that contain multiple simultaneous wavelengths in each beam. And, the output power at each wavelength can be kept constant as the combination of illumination wavelengths is changed. The combination of output wavelengths can be changed in less than 1 μsec, and a high-resolution spectrum of 600 $cm^{-1}$ span can be obtained in a fraction of 1 msec. Also, the disclosed spectrometer 10 can achieve a set of spatially distinguished spectra by moving its output beams 12 and the illuminated spot 16 observed by its photodetector, thereby producing a hyperspectral image.

The illuminating light is concentrated upon a small area 16 of the probed surface 15 at any given time and thus the standoff distance can be large.

In the prior art, an array of lasers have been used, however, in the prior art only one of the lasers in the array is activated at any one time. In contrast, the spectrometer 10 of the present disclosure activates simultaneously multiple lasers 46 of the array of laser devices 42. In the present disclosure, the various outputs of the multiple lasers 46 are modulated with unique RF tones 56, which enable the multiple wavelengths of photodetected light that originated from these multiple wavelengths of RF-modulated light to be distinguished from each other. Each wavelength is associated with its unique RF modulation tone 56.

The spectrometer 10 of the present disclosure may use semiconductor optical amplifiers (SOAs) for the optical amplifier/modulators 44. The direct current (DC) drive current to the SOA sets the time-average output power and the alternating current (AC) drive current achieves the RF modulation 56 of the optical output.

Further, the spectrometer 10 of the present disclosure may contain multiple arrays of laser devices 42 with each laser device 42 for each of the lasers in the multiple arrays of laser devices 42 having a laser section 46 emitting single-wavelength laser light and an optical amplifier/modulator section 44 that amplifies and modulates the laser light. Each array of multiple laser devices provides multi-wavelength light for a different Transmit beam 110.

In the sensor 10 of the present disclosure multiple Tx beams 110 may be combined or overlapped on the probed surface 15. The overlapped spot 16 can be illuminated with much higher power and the overlapped spot 16 also can be probed with more simultaneous wavelengths compared to the light provided by prior art active spectrometers, which produce only a single beam of light. The size of each Tx aperture that transmits as Transmit beam can be determined according to constraints that may be imposed, such as the need to keep the total output power from a given Tx aperture below the eye-safe level. Although the light exiting each Tx aperture 110 is continuous, or quasi-continuous long pulses, and has sinusoidal modulation of the intensity, the light illuminating a given area 16 on the probed surface 15 has only a short dwell time because the illuminating spot 16 is moved. Thus, even higher power-densities can be achieved at the probed surface 15 and still maintain eye safety.

FIG. 1 shows an active spectrometer 10 according to the present disclosure that illuminates a spot 16 on a probed surface 15 with multiple beams of multi-wavelength light 12, steers that spot of light to various locations on the probed surface 15, and collects, through its front aperture 20, the back-scattered or reflected light 18 from only the illuminated spot 16 and then provides an output indicating the amount of collected and detected light at only those wavelengths in common with the multi-wavelength illumination 12. For each wavelength of the illuminating light 12, the sensor provides an output 45, as shown in FIG. 2, corresponding to the amount of detected back-scattered or reflected light at that wavelength. Light from areas outside the illuminated spot 16 is not detected. Also, detected light that is of wavelengths other than those in the illuminating beams 12 are excluded from the outputs 45 of the sensor 10. The sensor 10 can change the pattern of illumination wavelengths 12, and thus the pattern of detected and output wavelengths, from one instance to the next and from one location of the probed surface 15 to the next. The wavelengths can cover a very large spectral span, such as a span of 600-800 $cm^{-1}$ in the LWIR range.

The block diagram shown in FIG. 2 depicts some of the optical and electrical components in the sensor 10, which may be optically or electronically coupled. The sensor 10 has a multi-wavelength optical source or transmitter 30 that produces multi-wavelength laser Transmit (Tx) light from an array of lasers 42 and combines those multiple wavelengths into one or more optical beams 12. The sensor 10 also has a multi-wavelength receiver 32 that receives and detects multi-wavelength Receive (Rx) light and distinguishes between the information contained in those multiple wavelengths of light. In the embodiment depicted in the FIG. 2, both the Tx light and the Rx light are coupled, in opposite directions, to a beam steering mirror 34 that directs the Tx light 12 to the illuminated spot 16 on the probed surface 15 and that directs the back-scattered and reflected light 18 collected from the illuminated spot 16 to one or more photodetectors 36 in the receiver 32. Both the Tx light and the Rx light are coupled, again in opposite directions, through a telescope system 38 between the beam steering mirror 34 and a focusing window 40 of the sensor 10, through which the respective Tx/Rx light pass to/from the probed surface 15.

As shown in FIG. 2, the transmitter 30 has an array of lasers and optical amplifiers/modulators 28 whose output is sent through a collimating lens, which may include a micro-lens array 122 and a collimating objective lens 150. The output of the collimating lens is then coupled to a grating wavelength combiner 152, whose output then may be sent through a beam-width transforming relay lens having a collimating objective lens 154 and an objective lens 156.

The receiver 32 has a corresponding objective lens 158 and a collimating objective lens 160, whose output goes to a local oscillator (LO) beam combiner 162, whose output is sent though a focusing objective lens 164. The focused light is then sent through cold stop 130 and cold shield 133 to photodetector 36. The output 37 of the photodetector 36 is connected to a transimpedance amplifier (TIA) 39 and an analog to digital converter 29 and then channelized and band pass filtered by channelizer and band pass filter 41 to produce output 45.

The output from transmitter 30 and the input to receiver 32 both are coupled to transmit/receive splitter 136 and to beam steering mirror 34, which is coupled to a beam-width transforming lens system 172 and telescope system 38, to provide transmit beams 12 to the illuminated spot 16 on the probed surface 15, and to receive reflected light 18 from the illuminated spot 16 on the probed surface 15.

The beam-width transforming lens system 172 may include focusing and collimating objective lens 174, field corrector lens 94, secondary reflective lens 92 and primary reflective lens 90. The telescope system 38 may include the field corrector lens 94, the secondary reflective lens 92, the primary reflective lens 90, and zoom-focusing window 40.

The sensor 10 is based on an array of laser devices 28, as shown in FIG. 3. The array of laser devices includes multiple single-wavelength emitting lasers 42, whose wavelengths are tunable, integrated with corresponding optical amplifiers/modulators 44. For operation at LWIR wavelengths (generally between 6 μm and 12 μm), the laser devices 42 can be realized using quantum cascade laser structures. Each laser device 42 has several sections of the quantum cascade laser structure, which can have the same basic quantum cascade material structure in their laser-core or active layer. Thus, the spectral profiles of the optical gain of these sections are approximately the same. One section of the laser devices 42 is a distributed feedback (DFB) laser 46 that also has a grating pattern etched into a grating layer that is adjacent to the active layer, which is described in References [5] and [8], listed above, which are incorporated herein by reference. Different laser devices 46 of the array 28 may have gratings of different periods so that the different laser devices emit light of different nominal wavelengths. The other sections do not have any grating pattern etched into their grating layer. A second section of each laser device is the optical amplifier/modulator 44. The combination of DFB laser 46 and optical amplifier/modulator 44 functions as a master oscillator, namely the DFB laser 46, that determines the wavelength of the emitted light and a power amplifier, namely the optical amplifier/modulator 44, that increases the output power of that light as described in Reference [9], listed above, which is incorporated herein by reference. In some embodiments, each laser device 42 also includes a third section that is an optical amplifier configured as a shutter or as on/off, output-enabling switch 48. When sufficient drive current from the laser array controller 50 is applied to an output-enabling switch 48 section, the section becomes transparent to the laser light and transmits that light through it. However, when low or zero current is applied to an output-enabling switch 48 section, the section absorbs and thus attenuates the light instead of transmitting it. In some embodiments, each laser device also includes another section, located on the opposite end of the DFB laser 46 section from the optical amplifier/modulator 44 section that is an optical amplifier configured as a variable attenuator 52. The drive current to the variable attenuator 52 section from the laser array controller 50 can be varied to change the attenuation of the laser light by this section. The drive current to the DFB laser 46 section from the laser array controller 50 can be adjusted to fine-tune the wavelength of the light emitted by that DFB laser 46. For typical LWIR quantum cascade DFB lasers 46, the emission wavelength can be tuned over 5-10 $cm^{-1}$ by changing the drive current.

The drives from the laser array controller 50 to each laser device 42 may be different.

Unlike prior combinations of DFB lasers and optical amplifiers that are monolithically integrated on the same growth substrate, the optical amplifier/modulators 44 of the disclosed array have in addition to a constant or continuous-wave (CW) drive current 54, a radio-frequency (RF) time-varying drive current 56. When the wavelength of the light emitted by the DFB laser 46 section is tuned by changing the drive current to that laser DFB 46 section, the intensity of the laser light coupled into the optical amplifier/modulator 44 section can change. The CW drive current 54 to the optical amplifier/modulator 44 can be adjusted to keep the time-average output power from the primary output 58 of the laser device 42 the same despite tuning of the laser wavelength. Furthermore, the CW drive current 54 to the optical amplifier/modulator 44 of the various laser devices 42 in an array can be adjusted to set the time-average power from the primary output 58 of those various laser devices 42 the same. The different laser devices 42 in an array may emit light of different wavelengths. It is beneficial for many spectrometry applications to have the same power emitted at the various different illumination wavelengths being measured by the spectrometer 10.

Figures 4A, 4B:
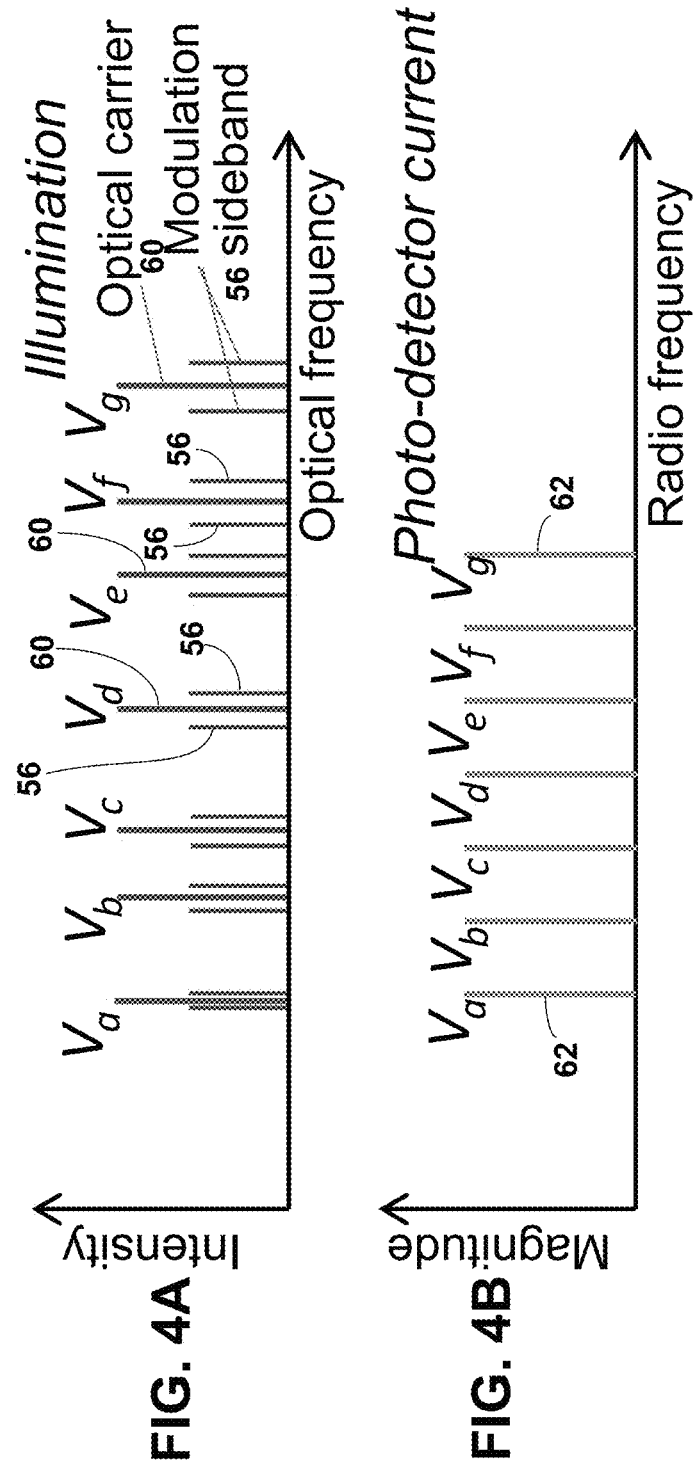
FIG. 4A shows an illustration of the optical spectrum of the illumination light produced by the sensor and FIG. 4B shows the radio frequency (RF) spectrum of the electrical output from a photodetector in the sensor in accordance with the present disclosure.

As shown in FIG. 4A, the RF tones 56 modulating the collection of optical amplifier/modulators 44 of the sensor 10 produce an optical spectrum that contains a set of optical-carrier spectral peaks 60 at the various illumination wavelengths or optical frequencies or wavenumbers, as well as their corresponding RF modulation-sidebands 56. For some applications, all of the laser devices 42 in an array may be activated. For other applications, only some of the laser devices 42 in an array may be activated and the combination of activated laser devices 42, and thus the pattern of laser wavelengths emitted from the Tx apertures, may be changed from measurement to measurement. In one embodiment, an RF tone 56 of a specific frequency is assigned to each laser device 42 of the array. Thus, each laser wavelength 60 of the multiple, different laser wavelengths that may be output simultaneously from the arrays has a unique and distinct RF tone 56 associated with it. As shown in FIG. 4A, each laser wavelength 60 has a different RF modulation sideband 56 due to the unique RF tone 56 modulation associated with each laser wavelength 60. In another embodiment, an RF tone 56 of a specific frequency is assigned to each laser device 42 of the array that is activated at a given time and is providing light included in the primary output from the array and thus included in the illuminated spot 16 on the probed surface 15. Thus, each laser wavelength 60 of the multiple, different laser wavelengths that are actually illuminating a probed surface 15 at a given time has a unique and distinct RF tone 56 associated with it.

The sensor 10 includes a photodetector 36 that detects the light 18 reflected or back-scattered from the illuminated spot 16, collected by the sensor Rx aperture and coupled to the photodetector 36. The photodetector produces a photo-current that is proportional to the intensity of the light. Thus, the photo-current is proportional to the square of the optical-field amplitude at the photodetector 36. The frequency response characteristic of the photodetector output current has a bandwidth that is in the RF band, as shown in FIG. 4B. The spectrum of the photodetector output waveform is a set of RF tones 62 obtained from the multiplication of the electric-fields of the optical carriers 60 and their associated RF modulation sidebands 56. Since the frequency spacing between an optical carrier 60 and its RF modulation sidebands 56 is the frequency of the RF tone 56 modulating that wavelength of light, the photodetector output 37 is a set of RF tones 62, as shown in FIG. 4B, that correspond directly with the set of optical wavelengths of the amplifier/modulator sections 44 modulated with the RF tones 56. As a result, there is a one-to-one correspondence between an optical wavelength in the illuminated spot 16 and an RF tone 62 in the photo-current for the light collected from that illuminated spot 16.

The array for a given Tx module, associated with a given Tx aperture and Transmit beam, can be a set of laser devices 42 that are fabricated on a single substrate 74 or laser devices 42 that are fabricated on several different substrates 74, as shown in FIGS. 7A and 7B. In most cases that involve multiple substrates, those substrates 74, each containing usually several laser devices 42, are mounted together on a common sub-mount 76. By using multiple substrates 74 instead of only one substrate of laser and one laser active-layer design to produce the multi-wavelength light, the design of the active layer in the laser structure of each substrate can be optimized for efficient lasing operation at a given, smaller range of wavenumbers and yet the array can cover a larger range of wavenumbers.

FIGS. 5A and 5B show some examples of the avenumber ranges for the various active-layer designs. Note that the examples shown cover both the LWIR and MWIR span and especially include wavenumbers that correspond to spectral signatures associated with molecular rotational and vibrational resonances of various chemicals of interest.

Figure 6:
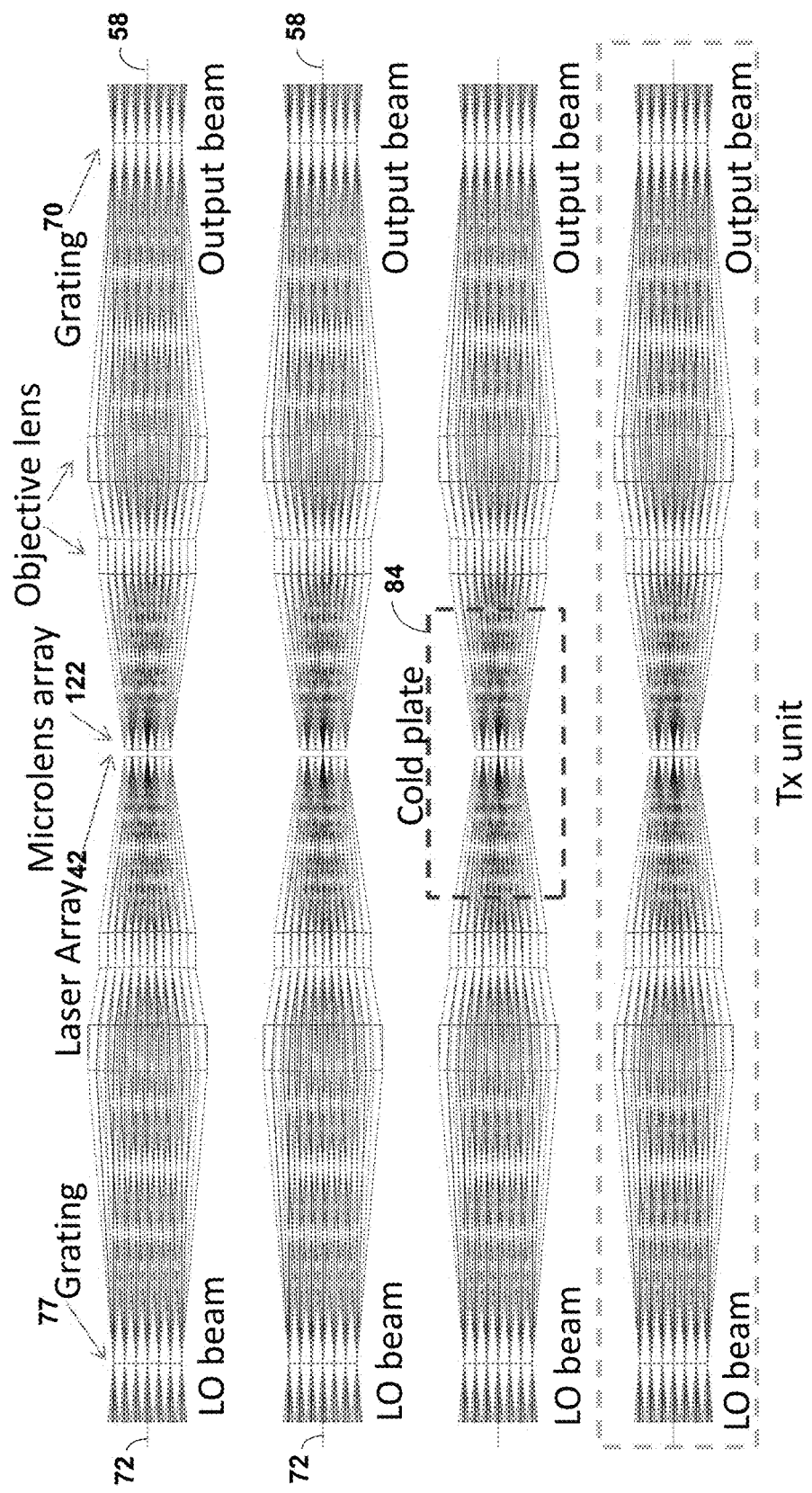
FIG. 6 shows multiple transmit (Tx) units, with each Tx unit containing a multi-wavelength array of laser devices and producing a multi-wavelength output beam in accordance with the present disclosure.

In a preferred embodiment, each laser device 42 of an array emits a beam of light whose wavenumber can be within a limited range of wavenumbers. Different laser devices 42 emit light of different wavenumber values as determined by the DFB laser 46 grating in that laser device 42. The multiple beams of laser light from the multiple laser devices 42 in an array are combined into a single multi-wavenumber beam by a grating 70, as illustrated in FIG. 6. For some embodiments, the laser devices of an array have a fixed spatial spacing 75. In some of these embodiments, the nominal values of the wavelengths of the light emitted by the various laser devices 42 on a given substrate 74 have a fixed increment, such as illustrated in FIG. 5B. However, laser devices 42 from different substrates 74 may have different wavelength increments, with the wavelength increment being larger for laser devices 42 emitting at shorter wavelengths. For some embodiments, the nominal values of the wavenumbers of the light emitted by the various laser devices of an array are separated by a fixed increment, as shown in FIG. 5A. In some of these embodiments, the devices on different substrates have different values of the spatial spacing 75 between adjacent laser devices 42, with the spatial spacing being larger for devices emitting at shorter wavelengths. These designs compensate for the non-linear dispersion of the wavelength-combining grating, which can degrade the overlap of the different wavelengths in the combined beam if those wavelengths cover a very large span. In general, the multiple substrates 74 contained in a given Tx module may have wavenumber or wavelength ranges that are adjacent to each other, which makes the design of the wavelength-combining grating element, discussed later, more relaxed.

In some embodiments, the sensor 10 includes several Transmit (Tx) modules with different Tx modules covering different ranges of wavenumbers. For example, one Tx module may include laser devices 42 of laser designs 1, 2 and 3 of FIG. 5A. Another Tx module may include laser devices 42 of laser designs 3, 4 and 5 of FIG. 5A. Yet another Tx module may include laser devices 42 of laser designs 6, 7 and 8 of FIG. 5A and another module may include devices of laser designs 9 and 10 of FIG. 5A. The multiple beams of light for each of the different Tx modules or Tx units may be coupled by different gratings 70, as illustrated in FIG. 6. This modular architecture allows the sensor capabilities to be tailored and optimized to a particular system need. For example, a sensor 10 may be tailored for spectral coverage and/or spectral resolution as required to meet the chemical identification needs of the target surface and application.

Each laser array may emit light from two opposite ends of the array. The primary output beam 58 of a Tx unit is directed to the front aperture 20 of the sensor 10 and to the probed surface 15, as shown in FIGS. 1 and 3. In some embodiments, a secondary, reference beam of a Tx unit, also called the local-oscillator (LO) beam 72, is directed to the photodetector 36 in the sensor 10. Variable attenuators 73 may be used to adjust the amplitude of the local-oscillator (LO) beams 72.

The array of laser devices 42 in a Tx unit can be mounted on a sub-mount 76, as shown in FIG. 7A. In a preferred embodiment, for which the array contains multiple laser devices 42 formed on multiple substrates 74, the multiple substrates 74 are mounted on the same sub-mount 76, as shown in FIG. 7A. In some embodiments, the sub-mount 76 has a stacked structure, as illustrated in FIG. 7A, and provides multiple functions. This stacked structure is preferably made from multiple layers of a material that has high thermal conductivity and low electrical conductivity, such as diamond. As depicted in FIGS. 7A and 7B, the top layer 78 of the structure has a first surface 81 that abuts the laser devices 42 formed on the multiple substrates 74. This first surface 81 may contain a pattern of metal interconnect lines 80 that are electrically coupled to multiple electrical contacts of the various laser devices 42. This first surface 81 may also contain a set of probe or bonding pads. The top layer 78, which may also be a heat spreading interposer 78, may also contain a set of via-holes 82 that are filled or covered with metal, so that those via-holes 82 can conduct electricity. The top layer 78 has a second surface, opposite the first surface, that may have a pattern of metal interconnect lines 83 between pairs of via-holes. The combination of the metal interconnect-lines 80 and 83 on the two surfaces and the via-holes 82 provide electrical interconnections between the pads and the electrical contacts of the laser devices 42 mounted on the top layer 78 of the sub-mount 76. The stack of layers in the sub-mount provides effective conduction of heat from the laser devices 42 to a cold plate 84 onto which the sub-mount 76 is mounted. The sub-mount 76 also provides effective lateral spreading of the heat and may include a heat spreader 86. The cold plate 84 may include structures such as fins or micro-channels for conducting fluids or air or other medium for removing heat and also for establishing desired temperatures of the cold plate 84, the sub-mount top layer 78 and the laser devices 42. In another embodiment each laser device 42 may be on a separate substrate 74 mounted to a sub-mount 76, as shown in FIG. 7B.

Figure 8A:
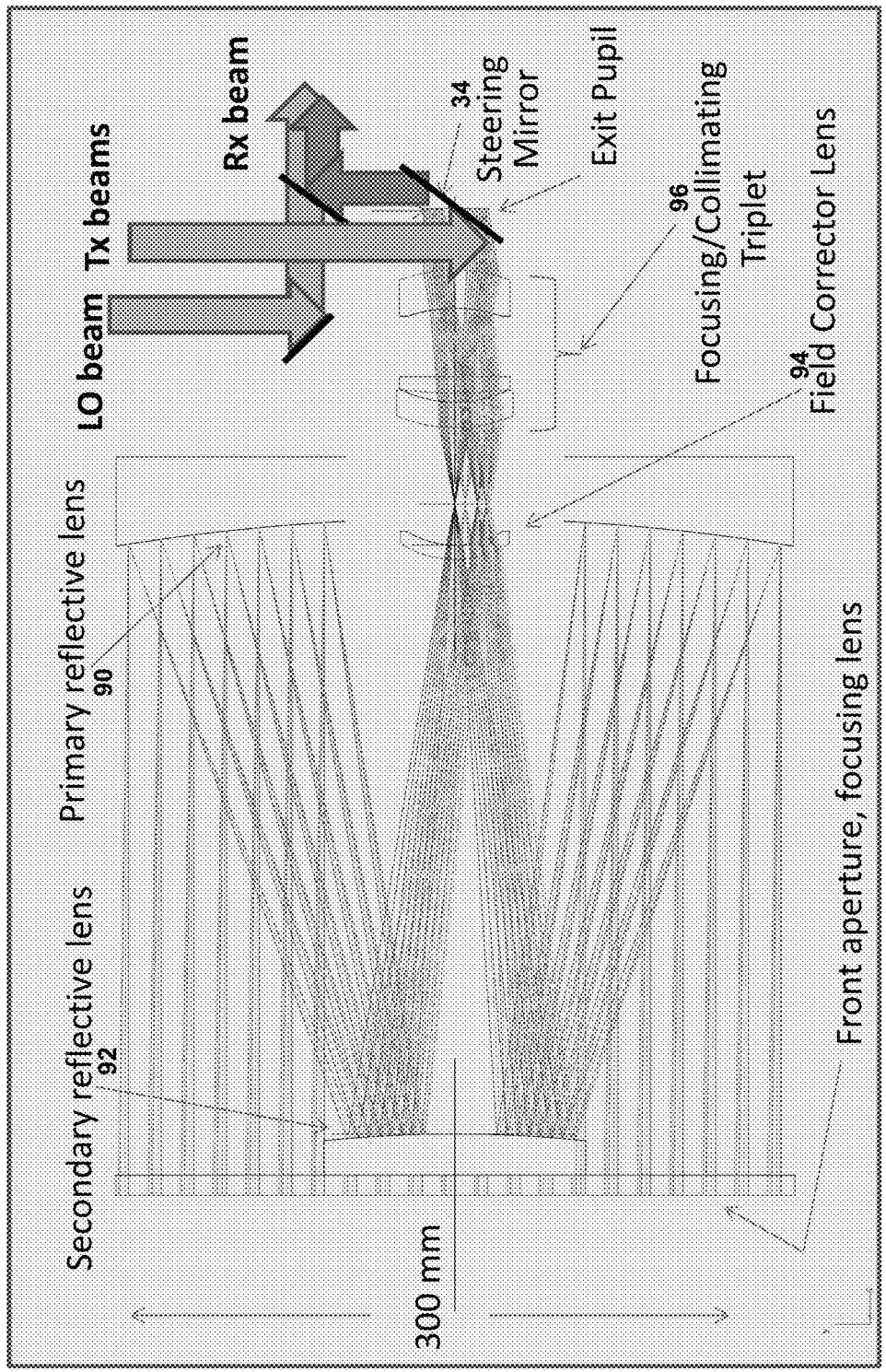
FIGS. 8A and 8B show a front-end telescope in the sensor coupling light to/from a beam-steering mirror in accordance with the present disclosure.
Figure 8B:
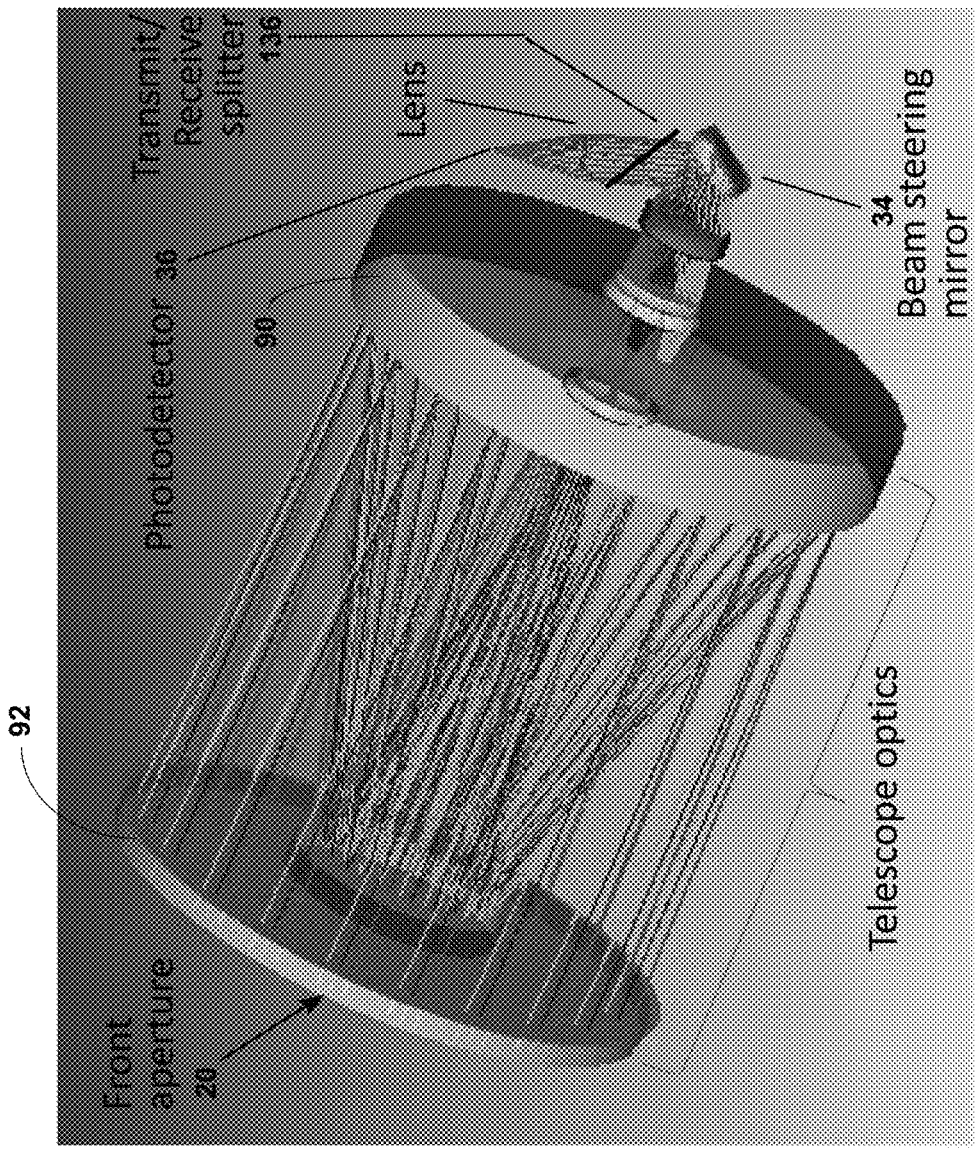

Some embodiments of the sensor may include a telescope that directs light to/from the sensor 10 and the probed surface 15 and couple that light from the laser devices 42 and to the photodetector 37. FIGS. 8A and 8B show an example of the telescope that includes a primary reflector 90 and a secondary reflector 92 arranged in a Cassegrain configuration as well as a refractive field-corrector lens 94. The secondary reflector 92 forms an occlusion at the center of the window or front aperture 20 of the sensor 10. The effective area of the aperture is the annulus that is between the secondary reflector 92 and the perimeter of the window. The window at the front aperture 20 actually can be a single-element or multi-element lens and the spacing between those elements can be changed to provide a zoom function. The sensor also includes a collimating/focusing objective lens 96 and a beam-steering mirror 34, as depicted in FIG. 8A. This objective lens in combination with the focusing window establishes a focal point located at the probed surface, for various standoff distances between the probed surface and the window of the sensor. In this embodiment, both the Tx beams and the Rx beam share the same steering mirror 34. This design ensures that it is the light from the Tx-illuminated spot 16 on the probed surface 15 that is coupled to the photodetector 36 as the Rx beam. A Transmit/Receiver splitter mirror 136, as shown in FIG. 8B, directs some of the light received from the probed surface to the photodetector 36 as the Rx beam. But some of the received light is not directed by the splitter mirror 136 toward the photodetector 36 but rather is coupled toward the laser devices 42. The grating in a Tx unit then selectively couples only the received light of the same wavelength as the laser light of a given laser device 42 back to that laser device 42. But the received light is generally quite weak compared to the Transmit light, as discussed later, and is not expected to degrade the quality of the emission from the DFB laser section 46. In some designs, the Transmit/Receive splitter mirror 136 may reflect the Receive light, as shown in the drawing of FIG. 8A. In other designs, the Transmit/ Receive splitter mirror 136 may reflect the Transmit light, as shown in the drawing of FIG. 8B. FIG. 8B illustrates how light from three different incidence angles may be coupled to the same photodetector 36 by suitably moving the beam-steering mirror 34.

Figure 11A:
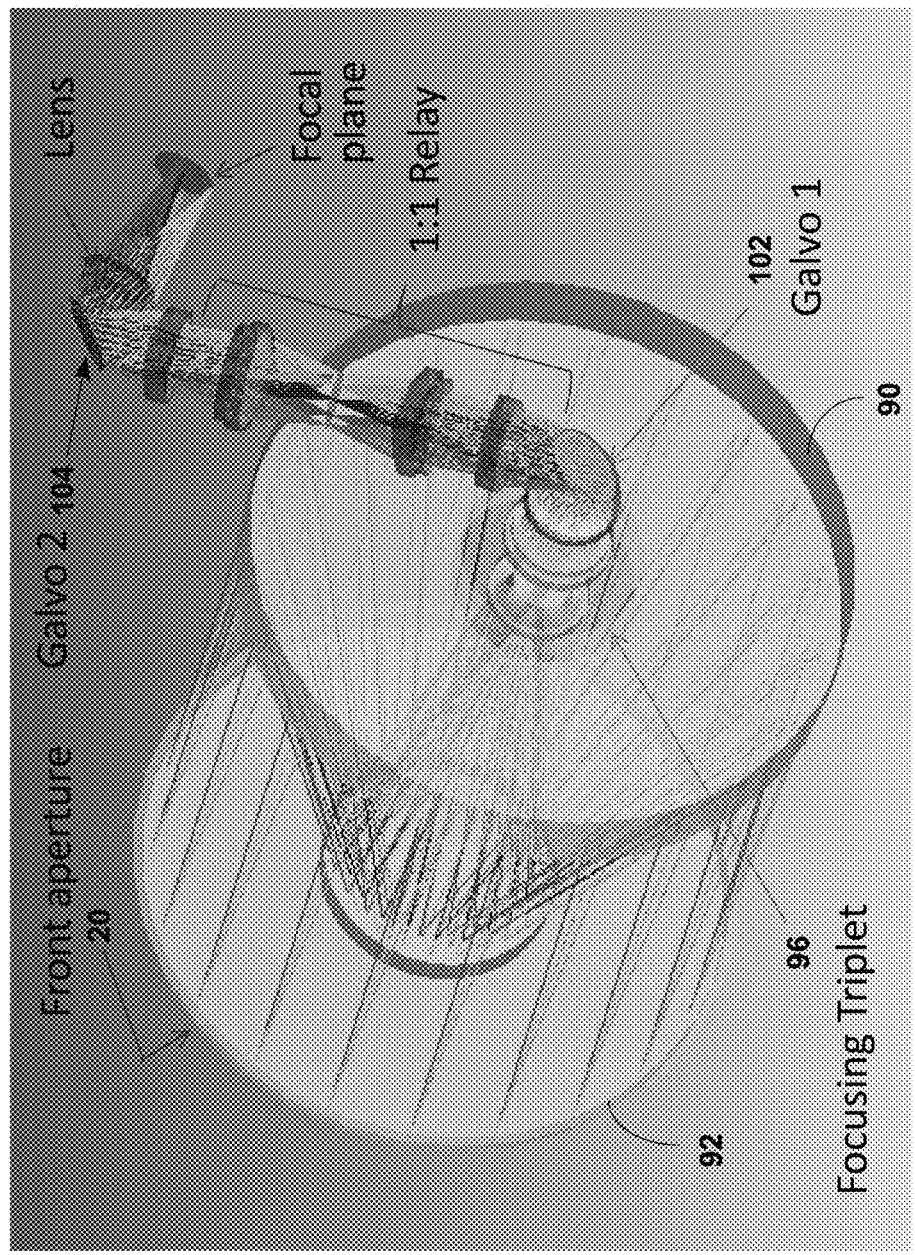
FIGS. 11A and 11B show the optical receiver operation of the sensor showing in FIG. 11A beam steering with a pair of one-axis-motion galvo mirrors and in FIG. 11B beam steering with a single two-axis-motion fast-steering mirror (FSM) in accordance with the present disclosure.
Figure 11B:
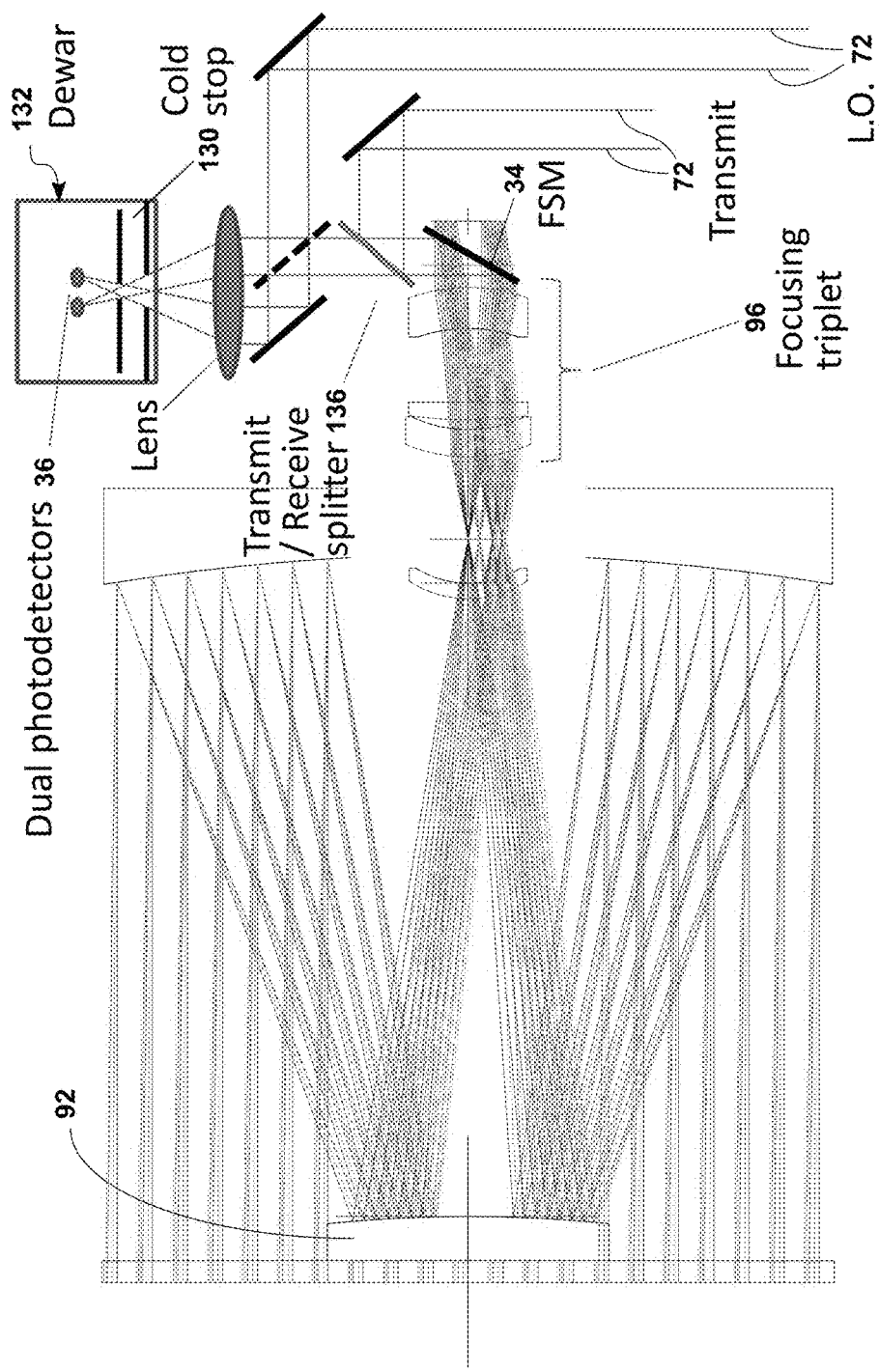

The beam-steering mirror 34 may be implemented as a single fast-steering mirror (FSM), as depicted in FIGS. 8A and 11B, which has movement in two orthogonal axes. This two-axis movement allows the beams to be steered in both elevation and azimuth, for example.

Figure 9A:
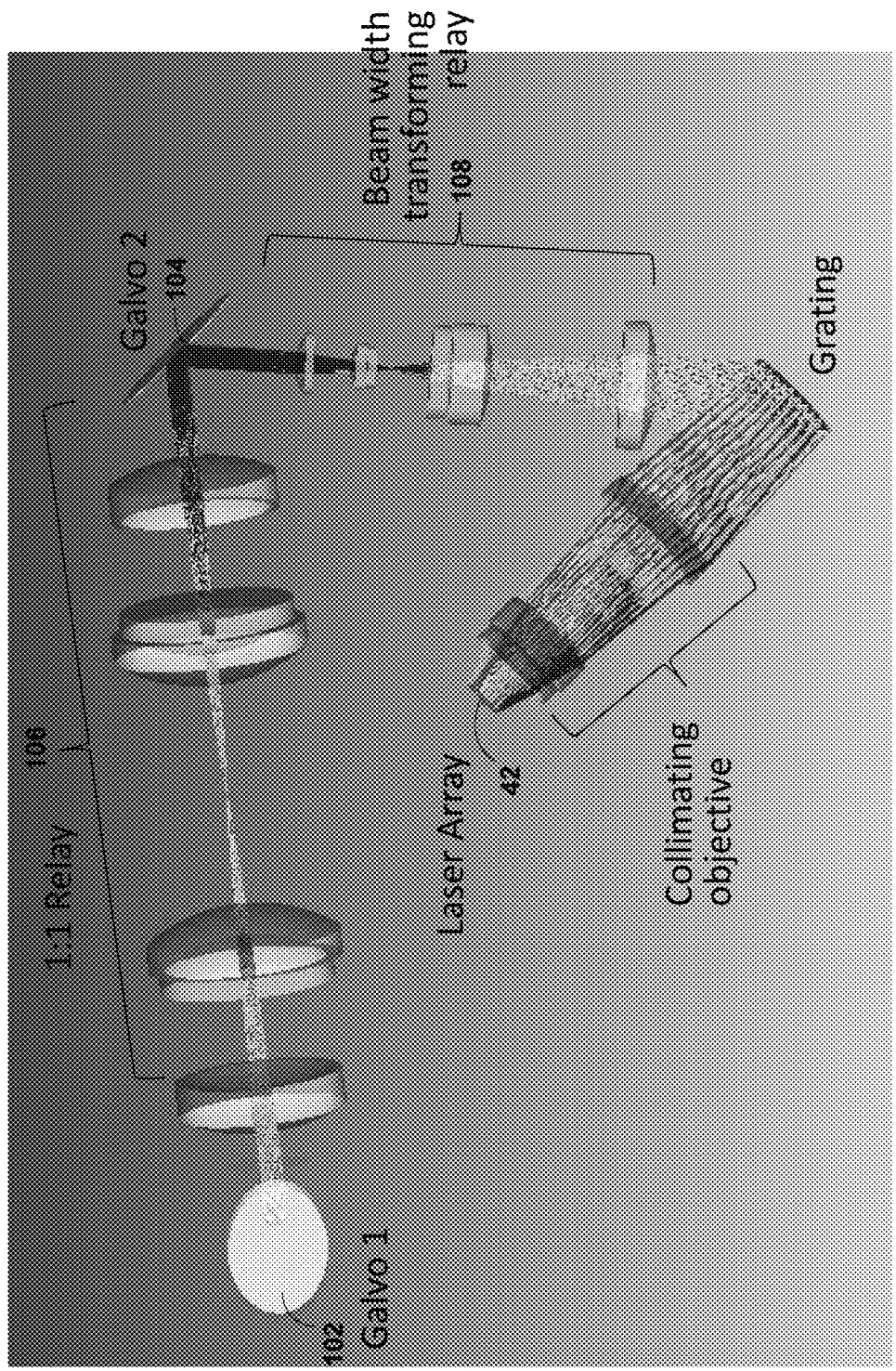
FIGS. 9A and 9B show an optical transmitter operation of the sensor, showing the light paths for one Tx unit in accordance with the present disclosure.
Figure 9B:
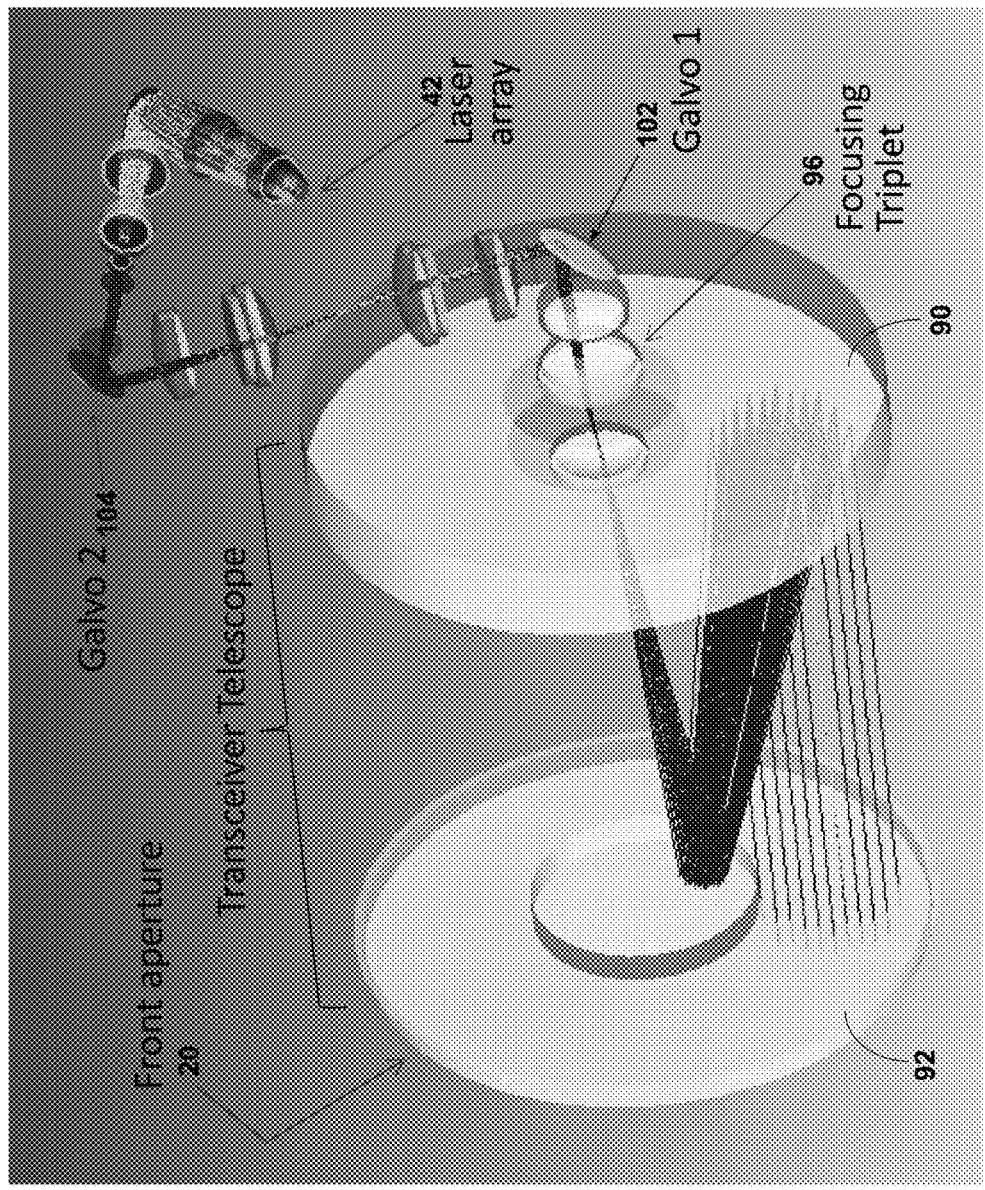

In some embodiments, the beam-steering mirror is implemented as a cascade of two single-axis steering mirrors, such a galvo mirrors 102 and 104, shown in FIGS. 9A and 9B. A pair of objective lens 106 can be used between the two mirrors to keep the beams from expanding and thus the sizes of the two mirrors can be kept the same. The drawings in FIGS. 9A and 9B also show additional optical components 108 associated with a Tx unit that resize and collimate the multi-wavelength beam from the grating of the Tx unit to fit within the size of the steering mirrors. As illustrated in FIG. 9B, the output Tx beam for a given Tx unit or Tx module occupies only a portion of the overall window or front aperture 20 of the sensor 10.

Incorporation of the beam-steering mechanism 34 before the front-end optics, or pre-objective location of the beam steering mirrors 34, enables rapid steering of the illuminated and observed spot 16, but with limited field of regard. The sensor may be augmented with post-objective beam steering such as mounting on a pan/tilt head or in a gimbal or adding a large steering mirror to increase the field of regard.

FIG. 10A shows an exemplary arrangement of 4 Tx output beams 110 at the front aperture 20 of the sensor 10. These 4 Tx beams 110 form 4 Tx apertures 110. The size of these Tx apertures 110 determines the size of the diffraction-limited focused spot 16 formed at the probed surface 15. The optical system of the sensor can be designed to have the light from all of the Tx apertures 110 focused, ideally, onto the same spot 16 at the probed surface 15. This can occur when all of the laser devices 42 emit light at the nominal wave-number associated with those laser devices 42. In actual practice, some of the laser devices 42 may have their DFB laser 46 sections tuned to emit light whose wavenumber are different from the nominal values. As a result, the gratings may slightly displace the portions of the Tx beams 120 associated with those particular wavenumbers, as illustrated in FIG. 10B. This results in the illuminated spot 16 at the probed surface 15 for those wavenumbers being displaced from the area observed by the photodetector 36. One way to ensure that the area observed by the photodetector 36 always is illuminated by all the selected wavelengths of the Tx light is to oversize the Tx beams 120 along the direction in which the tuning-related displacement occurs. This shaping of the Tx beams 120 can be accomplished by suitable design of the microlenses 122 coupled to the laser devices 42, as shown in FIG. 7A, and/or by some of the other optical components in the optical path of the Transmit light.

The Receive light 18 from the probed surface 15 is collected by the portion of the entire aperture 124, except for the central portion 126 that is occluded, as shown in FIGS. 10A and 10B.

The embodiment shown in FIG. 11A uses two galvo mirrors to accomplish the beam steering 34 in two orthogonal axes. The same telescope and focusing triplet and beam-steering mirror components are used for both the Transmit and the Receive light. A Transmit/Receive splitter mirror (not shown) may be located just after the second galvo mirror, for light traveling in the receive path. After the Transmit/Receive splitter mirror, the light to be coupled to the photodetector 36 is focused by a lens, through a cold stop 130 of a Dewar 132 and onto the photodetector 36 located at the focal plane. Light originating from different portions of the probed surface 15 may be incident on the front aperture 20 at slightly different angles. Those different portions of the incident light are focused onto slightly different locations on the focal plane of the lens, with the photodetector 36 being located on the focal plane. The size of the photodetector 36, as well as the size and placement of the cold-stop opening 134, can be set to allow only the light from the illuminated spot 16 on the probed surface 15 to be coupled onto the photodetector 36. For detection of MWIR and LWIR light, the photodetector 36 may have a reverse-biased PiN structure that is configured to suppress the dark current due to Auger processes and thereby improve the sensitivity of the sensor 10, as described in References [10] and [11], listed above, which are incorporated herein by reference. The output photocurrent is AC coupled to a transimpedance amplifier (TIA) 39 to remove the contributions that are not due to the illumination light, which is RF modulated.

In some embodiments, the receiver 32 is configured as a coherent receiver that combines the received light collected from the probed surface 15 with local oscillator (LO) light that is provided as the reference or LO beams 72 from the various laser devices 42 and then is wavelength-combined by gratings 77, shown in FIG. 6. Additional beam-splitters, generally including partially reflecting and partially transmitting mirrors, can be used to combine the multiple LO beams 72 from the multiple Tx units into a single LO beam that is then coupled to the photodetector 36.

FIG. 11B shows an embodiment of a coherent receiver that makes use of a pair of photodetectors 36. Such a balanced photodetector pair 36 can be configured in a differential manner to include the received light from the probed surface 15 that goes through both paths defined by the beam splitting mirror 136 but to cancel out the common-mode noise of the LO light, as described in Reference [12], listed above, which is incorporated herein by reference. As illustrated in FIG. 11B, both paths can go through the same cold stop 130.

Figure 12A:
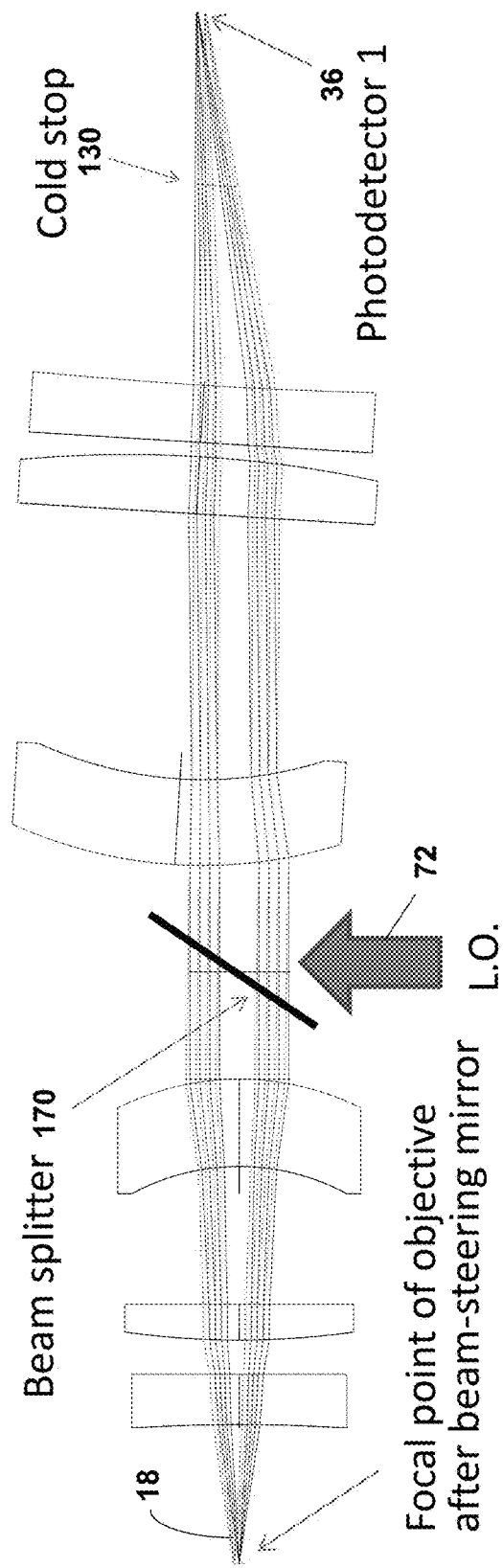
FIGS. 12A and 12B show the optical paths to both photodetectors of a coherent receiver configuration in accordance with the present disclosure.
Figure 12B:
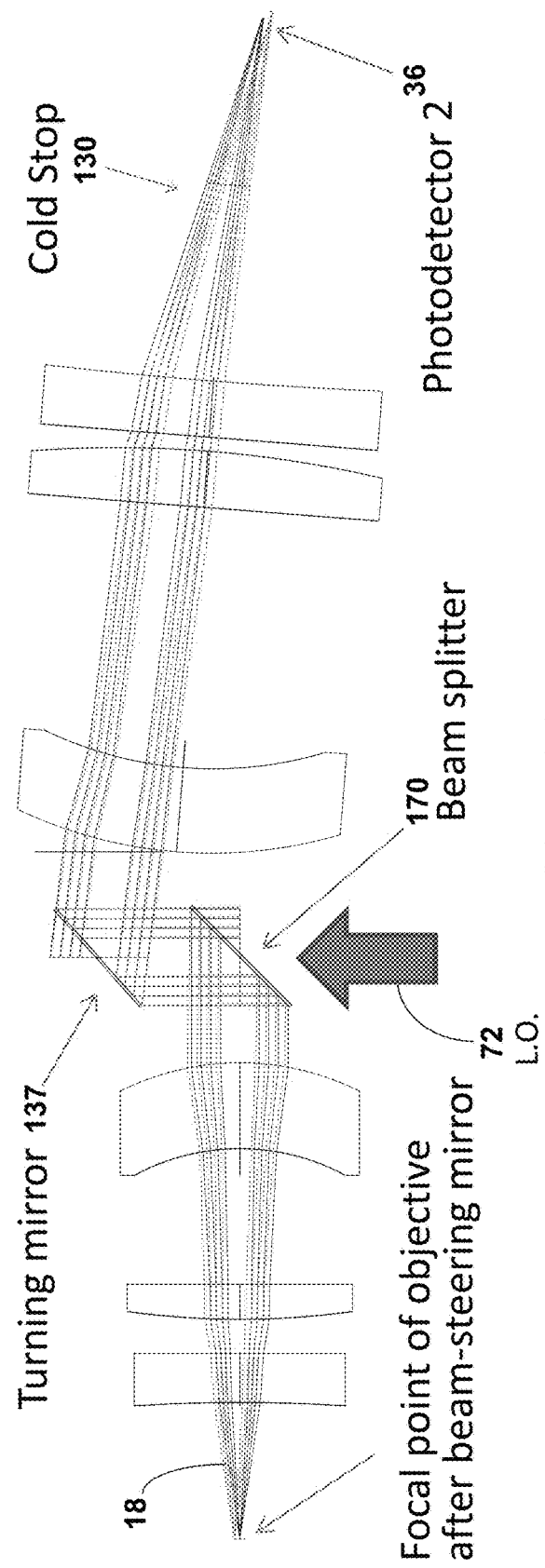

FIGS. 12A and 12B show the optical paths to both photodetectors 36 of a coherent receiver configuration in accordance with the present disclosure. Two additional objective lenses are used to achieve a collimated beam at the beam splitter that combines the beam of received light with the beam of LO light. FIG. 12A shows one path of the combined Receive light 18 and LO light 72 through the beam splitter/combiner 170. A second path of the combined Receive light 18 and LO light 72 goes through both the beam splitter/combiner 170 and a turning mirror 137, as shown in FIG. 12B. It is beneficial to keep small the distance between the beam splitter 170 and the turning mirror 137 adjacent to it, thereby minimizing the difference between the lengths of the two paths taken by the combined Receive 18 and LO 72 light. Having a smaller distance allows the dual-photodetector configuration to achieve cancellation of the LO laser noise over a larger frequency bandwidth.

A Cassegrain telescope design, like the one described above, can provide a large aperture for transmit and receive in a compact construction. The large aperture is beneficial for operation of the sensor at large standoff distances, since it is capable of collecting more received light and also obtaining a smaller diffraction-limited illuminated spot on the probed surface. For smaller standoff distances, a refractive optics design may be used in place of the telescope. An example of a refractive optics front-end 20 for the sensor 10 is shown in FIG. 13A. The refractive optical elements replace the primary and secondary reflectors and the field-corrector lens in the Cassegrain telescope designs shown in FIGS. 8A, 8B, 9A, 9B, 10A, 10B, 11A and 11B. The focusing/collimating objective, the beam-steering mirror and the various back-end components that are in the optical paths on the opposite side of the beam-steering mirror from the front-end elements still are present in the sensor configuration based on a refractive-optics front end. For a Cassegrain telescope, zoom focus can be achieved by moving the relative spacing between the primary mirror 90 and the secondary mirror 92 or by adding a two-element window. For a refractive-optics design, such as illustrated in FIG. 13A, one or more lenses 105 may be moved to accomplish the zoom-focus adjustment. This focus adjustment changes the size of the focused spot on the probed surface 15.

Figure 13B:
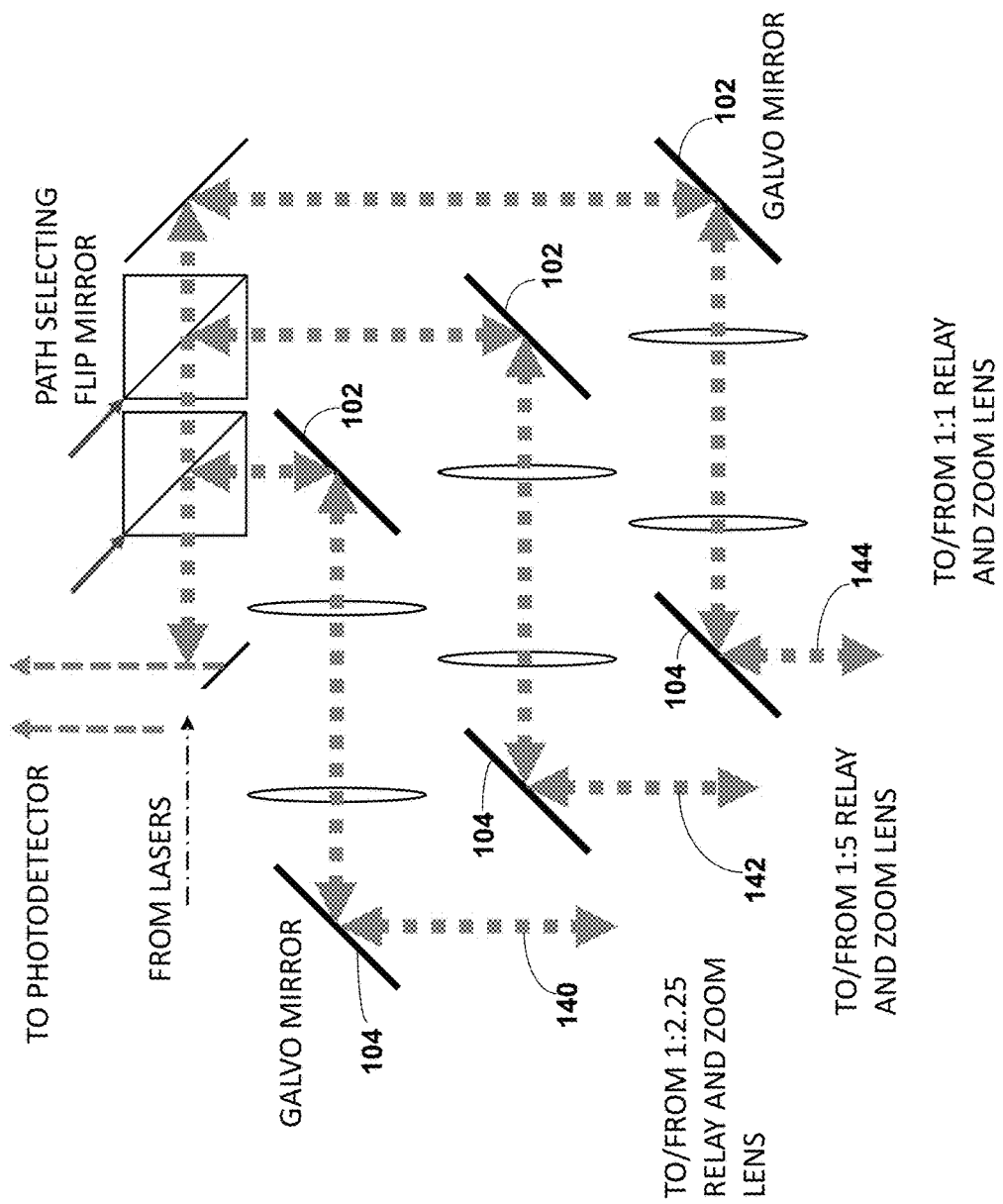

FIG. 13B shows a multi-aperture design that maintains the size of the illuminated and observed spot when the sensor must operate over a very large range of standoff distances. For example, a 10-to-1 variation in standoff distance might be achieved by using 3 separate apertures that each covers a zoom-focus range of approximately 2.5-to-1. One aperture 140 may have a 1:5 relay for the larger standoff distances of the overall range. Another aperture 142 may have a 1:2.25 relay for the intermediate standoff distances and yet another aperture 144 may have a 1:1 relay for the smallest standoff distances. Note that the size of the effective Tx apertures and also the net light-collecting area of the Rx aperture both become smaller as the relay scale is reduced from 1:5 to 1:1. Although FIG. 13B shows each of the 3 apertures as having separate sets of beam-steering mirrors, it also is possible to have one set of beam-steering mirrors for all 3 apertures, with those beam-steering mirrors located between the Tx/Rx splitter 136 and the path-selecting flip mirrors for the latter case.

The examples shown in FIGS. 13C, 13D and 13E are for a sensor that has 7 Tx apertures 110 located near the center of the overall aperture for ranges of 1000 MM, 925 MM and 1050 MM. Thus, the Tx/Rx splitter 136 may be implemented as a mirror that has a hole at its center to pass the Tx beams, with the Rx light for the photodetector 36 reflected by the outer portions of that mirror. The zoom-focus adjustment can be set to obtain a somewhat defocused spot 16 at the probed surface 15 for those standoff distances that are near the short-distance end of the standoff range for a given aperture, as shown in FIGS. 13D and 13E. This reduces the change in the size of the illuminated and observed spot as the standoff distance is varied.

The performance of the sensor 10 can be described in terms of the anticipated signal-to-noise ratio (SNR) that is obtained for each wavelength of the illuminating light 12. The SNR depends not only on the standoff distance but also on the relative reflectance or back-scattering efficiency for the light at that illumination wavelength. The reflectance or back-scattering efficiency will depend on factors such as the substrate material of the probed surface, the presence of chemical residues on that probed surface and the geometric arrangement of the measurement (such as the relative tilt angle between the surface and the sensor window).

Figure 14B:
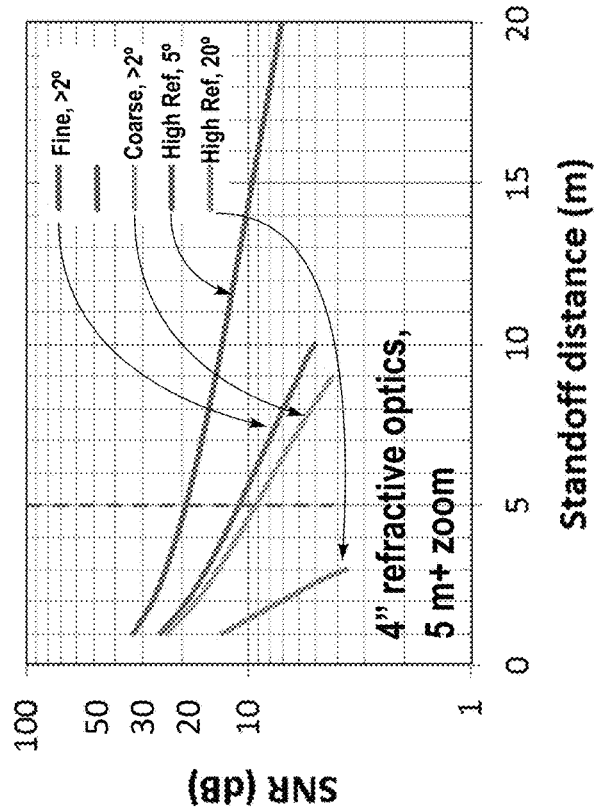
FIGS. 14A and 14B show the estimated signal-to-noise (SNR) performance of the sensor, for a large-aperture telescope front-end in FIG. 14A, and a smaller-aperture refractive optics front-end in FIG. 14B in accordance with the present disclosure.
Figure 14A:
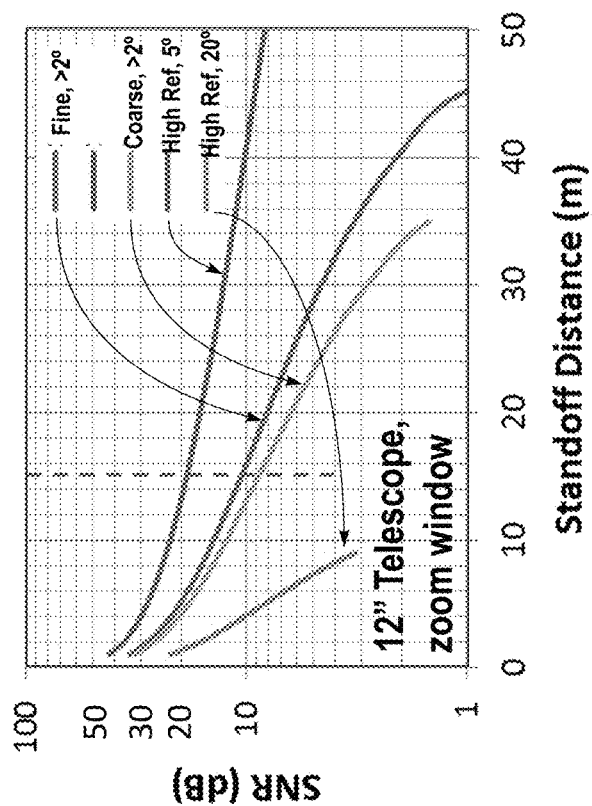

FIGS. 14A and 14B show plots of the anticipated SNR that may be achieved for several examples of substrate materials (such as high-reflectivity metal, a material with fine roughness such as wood, and a material with coarse roughness such as a duffel-bag covering) and for several examples of the relative tilt angle. The reflectance can vary substantially with the substrate material, as described in Reference [1], listed above, which is incorporated herein by reference, as well as with the relative tilt angle, as described in Reference [2], listed above, which is incorporated herein by reference. For these calculations, we estimated a CW laser power of 50 mW for each wavelength, which can be achieved for state-of-art quantum cascade lasers over the entire anticipated tuning ranges employed for each laser material design of the laser arrays. Also, we estimated a photodetector dark current of 0.3 µA, which can be achieved for state-of-art cryogenic cooled HgCdTe photodetectors.

For these estimates, we can assume the noise is limited by the photodetector dark current since most of the contributions from back-ground illumination and from thermal (black-body) emission are removed because the optical system is designed to couple to the photodetector only the light 18 from the illuminated spot 16 at the probed surface 15. Also, the cold shield 133 and cold stop 130 of the photodetector Dewar 132 block other light from being coupled onto the photodetector 36. The RF or alternating current (AC) coupling of the photodetector 36 removes the low-frequency noise and also the slowly varying background light that may happen to be at the illumination wavelengths. The bandpass filters (BPF) 41 in the receiver, whose center frequencies are aligned with the frequencies of the RF tones 56 modulating the laser devices 42, can remove much of the broadband noise associated with the laser devices 42, the photodetector 36 and the electronics. The channelizer and bandpass filters are shown in FIG. 2 as being implemented by an analog-to-digital converter (ADC) 39, a digital channelizer 41, which may be implemented with a field-programmable gate array (FPGA) or a processor, and a digital bandpass filter 41. However, these channelization and filtering functions also may be implemented by analog or mixed-signal circuits.

Although the laser power coupled onto the illuminated spot by the sensor is quite high, reflected or back-scattered light from the probed surface 15 typically is many orders of magnitude weaker. The reflectance of a highly reflective surface can drop from a value close to 1.0 for illuminating light at normal incidence to a value of 0.002 at 5 degree relative tilt and a value of only 0.00002 (or $2\times10^{-5}$) at 20 degree relative tilt, as described in Reference [2], listed above, which is incorporated herein by reference. The diffuse reflectance from rougher surfaces does not have such a large variation with the relative tilt angle once that tilt angle exceeds 1-2 degrees but the reflectance is much less than 0.001, as described in References [1] and [2], listed above, which are incorporated herein by reference.

The various features described above of the disclosed sensor enable it to increase the laser power in the illuminated spot, to increase the illuminated duration when a given overall area of a surface must be probed within a limited time, and to eliminate most of the contributions from noise and background light. As a result, the allowable standoff distance for the disclosed sensor can be larger by an order of magnitude or more than the standoff distances of prior active spectrometers.

Having now described the invention in accordance with the requirements of the patent statutes, those skilled in this art will understand how to make changes and modifications to the present invention to meet their specific requirements or conditions. Such changes and modifications may be made without departing from the scope and spirit of the invention as disclosed herein.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the step(s) of . . . ."

What is claimed is:

1. A sensor comprising:
a plurality of laser transmitter units, wherein each of the plurality of laser transmitter units is configured to transmit a light beam having a plurality of wavelengths;
a photodetector; and
an optical system coupled to the plurality of laser transmitter units and the photodetector;
wherein the optical system directs the light beam from each of the laser transmitter units onto a same illuminated spot on a probed surface; and
wherein the optical system collects light from the same illuminated spot and directs the light to the photodetector.

2. The sensor of claim 1 further comprising:
an aperture;
wherein the optical system directs the light beam from each respective laser transmitter unit onto a portion of the aperture different from portions of the aperture onto which other light beams from other laser transmitter units are directed.

3. The sensor of claim 2:
wherein the optical system directs the light beams from different portions of the aperture to the same illuminated spot on the probed surface; and
further comprising a beam steering device coupled to the optical system for moving a spatial position of the same illuminated spot on the probed surface, and for directing the collected light to the photodetector.

4. The sensor of claim 3:
wherein the beam steering device comprises at least one single two-axis-motion fast-steering mirror, or at least a pair of one-axis-motion galvo mirrors.

5. The sensor of claim 1:
wherein each of the transmitted wavelengths of the plurality of wavelengths transmitted by each laser transmitter unit is modulated by a radio frequency that is unique for each transmitted wavelength; and further comprising a channelizer coupled to the photodetector, the channelizer having a plurality of receiver outputs;
wherein each respective receiver output is derived using the radio frequency that is unique for each transmitted wavelength; and
wherein each respective receiver output corresponds to one of the transmitted wavelengths.

6. The sensor of claim 1 wherein each transmitted wavelength comprises a long-wave infrared (LWIR) wavelength, a mid-wave infrared (MWIR) wavelength, or a short-wave infrared (SWIR) wavelength.

7. A multi-spectral sensor comprising:
a plurality of laser devices each comprising:
a laser section having a light output;
an optical amplifier coupled to the laser section; and
an optical modulator coupled to the optical amplifier;
wherein the light output of each respective laser section of the plurality of laser devices has a respective wavelength that is different from a wavelength of the light output from each other laser section of the plurality of laser devices;
wherein each respective optical modulator of the plurality of laser devices is configured to modulate the light output of a respective laser section with a respective modulation frequency that is different from a modulation frequency of each other optical modulator of the plurality of laser devices; and
wherein the multi-spectral sensor is configured so that the plurality of laser devices simultaneously transmit a plurality of light beams, each respective light beam modulated with a respective modulation frequency; and
a photodetector for detecting received light; and
a channelizer coupled to the photodetector, the channelizer having a plurality of receiver outputs;
wherein each respective receiver output of the plurality of receiver outputs is derived using one of the respective modulation frequencies; and
wherein each respective receiver output corresponds to one of the respective wavelengths.

8. The multi-spectral sensor of claim 7:
wherein each respective laser section comprises a distributed feedback laser having a grating of a different grating period, or wherein each respective laser section comprises a distributed feedback laser having a different drive current.

9. The multi-spectral sensor of claim 7 further comprising:
a plurality of reference light outputs coupled between the plurality of laser devices and the channelizer;
wherein each respective reference light output has one of the respective wavelengths.

10. The multi-spectral sensor of claim 7 wherein each wavelength comprises a long-wave infrared (LWIR) wavelength, a mid-wave infrared (MWIR) wavelength, or a short-wave infrared (SWIR) wavelength.

11. The multi-spectral sensor of claim 7 wherein each modulation frequency is a radio frequency.

12. The multi-spectral sensor of claim 7 wherein the plurality of laser device comprises:
at least two first laser devices located adjacent to each other and separated by a first spatial spacing, wherein the at least two first laser devices each have a different wavelength, and wherein the different wavelengths of the at least two first laser devices are different by a first increment; and
at least two second laser devices located adjacent to each other and separated by a second spatial spacing, wherein the at least two second laser devices each have a different wavelength, and wherein the different wavelengths of the at least two second laser devices are different by a second increment;
wherein the first spacing and the second spacing are equal;
wherein the wavelengths of the two first laser devices are longer than the wavelengths of the second two laser devices; and
wherein first increment is smaller than the second increment.

13. The multi-spectral sensor of claim 7 further comprising:
an optical system for directing the plurality of light beams onto a same illuminated spot on a probed surface; and
a beam steering device coupled to the optical system for moving a spatial position of the same illuminated spot on the probed surface, and for directing the received light to the photodetector.

14. The multi-spectral sensor of claim 7 wherein the plurality of laser devices further comprises:
a laser array controller comprising:
a laser wavelength control coupled to each laser section for tuning the wavelength of each respective laser section;
an output level adjust coupled to each optical amplifier;
a radio frequency control coupled to each optical modulator.

15. The multi-spectral sensor of claim 7 further comprising:
at least a first substrate and a second substrate;
a first plurality of laser devices of the plurality of laser devices on the first substrate;
a second plurality of laser devices of the plurality of laser devices on the second substrate;
a top layer for providing interconnects for the first and second plurality of laser devices, wherein the first substrate and the second substrate are on the top layer;
a heat spreader coupled to the top layer; and
a cold plate coupled to the heat spreader.

16. The multi-spectral sensor of claim 13:
wherein the photodetector comprises a first photodetector and a second photodetector; and
wherein the optical system and the beam steering device direct the received light to the first photodetector and the second photodetector.

17. The multi-spectral sensor of claim 13:
wherein the beam steering device comprises a single two-axis-motion fast-steering mirror, or a pair of one-axis-motion galvo mirrors.

18. A method of sensing comprising:
simultaneously transmitting from each of a plurality of laser transmitter units a light beam, wherein each light beam comprises a plurality of wavelengths;
directing the light beam from each of the laser transmitter units onto a same illuminated spot on a probed surface using an optical system;
collecting light from the same illuminated spot and directing the collected light to a photodetector; and
detecting the collected light using the photodetector.

19. The method of claim 18 further comprising:
directing the light beam from each respective laser transmitter unit onto a portion of an aperture different from portions of the aperture onto which other light beams from other laser transmitter units are directed.

20. The method of claim 19 further comprising:
directing the light beams from different portions of the aperture to the same illuminated spot on the probed surface; and
steering the light beams using a beam steering device to move a spatial position of the same illuminated spot on the probed surface, and for directing the collected light to the photodetector.

21. The method of claim 20:
wherein the beam steering device comprises at least one single two-axis-motion fast-steering mirror, or at least a pair of one-axis-motion galvo mirrors.

22. The method of claim 18 further comprising:
modulating each of the transmitted wavelengths of the plurality of wavelengths transmitted by each laser transmitter unit by a radio frequency that is unique for each transmitted wavelength; and
channelizing an output of the photodetector to form a plurality of receiver outputs;
wherein each respective receiver output is derived using the radio frequency that is unique for each transmitted wavelength; and
wherein each respective receiver output corresponds to one of the transmitted wavelengths.

23. The method of claim 18 wherein each transmitted wavelength comprises a long-wave infrared (LWIR) wavelength, a mid-wave infrared (MWIR) wavelength, or a short-wave infrared (SWIR) wavelength.

* * * * *